United States Patent
Hua et al.

(10) Patent No.: US 12,192,285 B2
(45) Date of Patent: Jan. 7, 2025

(54) METHOD FOR MANAGING A PHYSICAL LAYER UTILIZED DURING A WIRELESS CONNECTION WITH MEDICAL DEVICES

(71) Applicant: ABBOTT DIABETES CARE INC., Alameda, CA (US)

(72) Inventors: Xuandong Hua, Mountain View, CA (US); Jean-Pierre Cole, Tracy, CA (US); Perry Li, Arcadia, CA (US); Souvik Dubey, Woodland Hills, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 381 days.

(21) Appl. No.: 17/736,586

(22) Filed: May 4, 2022

(65) Prior Publication Data
US 2022/0263904 A1 Aug. 18, 2022

Related U.S. Application Data

(63) Continuation-in-part of application No. 17/085,017, filed on Oct. 30, 2020, now Pat. No. 12,021,555.

(51) Int. Cl.
*H04B 7/00* (2006.01)
*A61N 1/372* (2006.01)
(Continued)

(52) U.S. Cl.
CPC .......... *H04L 67/12* (2013.01); *A61N 1/37276* (2013.01); *A61N 1/3756* (2013.01);
(Continued)

(58) Field of Classification Search
CPC ... H04L 67/12; H04L 1/0009; H04L 63/0428; H04L 63/0869; H04L 69/321;
(Continued)

(56) References Cited

U.S. PATENT DOCUMENTS

| 5,063,081 A | 11/1991 | Cozzette et al. |
| 5,294,404 A | 3/1994 | Grandone et al. |

(Continued)

FOREIGN PATENT DOCUMENTS

EP 2426865 A2 7/2012

OTHER PUBLICATIONS

Extended European Search Report for EP Application No. 21179178.5 dated Dec. 16, 2021 (5 pages).
(Continued)

*Primary Examiner* — Stephen M D Agosta
(74) *Attorney, Agent, or Firm* — Dean D. Small; The Small Patent Law Group, LLC

(57) ABSTRACT

Techniques include a medical device including processors, one or more sensors configured to generate signals corresponding to one or more physiological signals detected in a body of a user, a communication module configured to communicate wirelessly with a receiving device using a communication protocol capable of data transmission or reception at multiple data rates, and memories including instructions to cause the one or more processors to transmit information to the receiving device indicating that the communication module is configured to communicate using the multiple data rates; determine one of the data rates to be utilized for at least one of data transmission or reception during a communication session with the receiving device; initialize the communication session with the receiving device using the determined data rate; and transmit, via to the receiving device and using the determined data rate, communications based on the signals corresponding to the physiological signals.

34 Claims, 8 Drawing Sheets

(51) Int. Cl.
*A61N 1/375* (2006.01)
*H04B 1/401* (2015.01)
*H04B 7/26* (2006.01)
*H04L 1/00* (2006.01)
*H04L 67/12* (2022.01)
*H04B 1/3827* (2015.01)

(52) U.S. Cl.
CPC ........... *H04B 1/401* (2013.01); *H04B 7/2603* (2013.01); *H04L 1/0009* (2013.01); *H04B 1/3827* (2013.01); *H04B 2201/71346* (2013.01)

(58) Field of Classification Search
CPC ... H04L 69/323; H04L 1/0002; H04L 1/0025; H04L 67/125; A61N 1/37276; A61N 1/3756; A61N 1/36062; A61N 1/365; A61N 1/37282; A61B 5/0022; A61B 5/318; A61B 5/686; H04B 1/401; H04B 7/2603; H04B 1/3827; H04B 2201/71346
See application file for complete search history.

(56) References Cited

U.S. PATENT DOCUMENTS

| | | | |
|---|---|---|---|
| 5,562,713 A * | 10/1996 | Silvian | A61N 1/37252 |
| | | | 128/903 |
| 7,406,710 B1 | 7/2008 | Zellner et al. | |
| 7,419,821 B2 | 9/2008 | Davis et al. | |
| 7,583,649 B1 | 9/2009 | Bagchi | |
| 7,682,833 B2 | 3/2010 | Miller et al. | |
| 7,723,099 B2 | 5/2010 | Miller et al. | |
| 8,391,980 B2 | 3/2013 | Bornzin et al. | |
| 8,554,333 B2 | 10/2013 | Wu et al. | |
| 8,831,747 B1 | 9/2014 | Min et al. | |
| 8,923,773 B1 | 12/2014 | Gitlin et al. | |
| 9,044,610 B2 | 6/2015 | Rosenberg et al. | |
| 9,216,285 B1 | 12/2015 | Boling et al. | |
| 9,232,485 B2 | 1/2016 | Wu et al. | |
| 9,288,614 B1 | 3/2016 | Young et al. | |
| 9,333,351 B2 | 5/2016 | Arnold et al. | |
| 9,408,147 B2 | 8/2016 | Polo et al. | |
| 9,813,189 B2 | 11/2017 | Chou et al. | |
| 10,168,974 B2 | 1/2019 | Hampapuram et al. | |
| 10,182,336 B1 | 1/2019 | Stockton et al. | |
| 10,231,655 B2 | 3/2019 | Wedekind et al. | |
| 10,722,704 B2 | 7/2020 | Min et al. | |
| 10,765,860 B2 | 9/2020 | Min et al. | |
| 11,045,643 B2 | 6/2021 | Fischer et al. | |
| 11,083,372 B2 * | 8/2021 | Thakur | A61B 5/686 |
| 11,690,538 B2 | 7/2023 | Hernandez-Rosas et al. | |
| 2003/0114898 A1 | 6/2003 | Von Arx | |
| 2003/0216135 A1 | 11/2003 | McDaniel et al. | |
| 2004/0018577 A1 | 1/2004 | Emerson Campbell et al. | |
| 2004/0030260 A1 | 2/2004 | Arx | |
| 2004/0032882 A1 | 2/2004 | Kane | |
| 2006/0160534 A1 | 7/2006 | Jung et al. | |
| 2006/0161222 A1 * | 7/2006 | Haubrich | G16H 40/67 |
| | | | 607/32 |
| 2006/0241701 A1 | 10/2006 | Markowitz et al. | |
| 2006/0287693 A1 | 12/2006 | Kraft et al. | |
| 2007/0129045 A1 | 6/2007 | Aerrabotu | |
| 2007/0180047 A1 | 8/2007 | Dong et al. | |
| 2008/0086176 A1 | 4/2008 | Ofek | |
| 2008/0149659 A1 | 6/2008 | Dishongh et al. | |
| 2008/0240070 A1 | 10/2008 | Feher | |
| 2008/0281585 A1 | 11/2008 | Feher | |
| 2009/0016286 A1 | 1/2009 | Fajardo et al. | |
| 2009/0043360 A1 | 2/2009 | Doerr | |
| 2009/0247187 A1 | 10/2009 | Feher | |
| 2010/0198142 A1 | 8/2010 | Sloan et al. | |
| 2010/0260679 A1 | 10/2010 | Shachar et al. | |
| 2010/0297941 A1 | 11/2010 | Doan et al. | |
| 2010/0317289 A1 | 12/2010 | Desai et al. | |
| 2011/0160544 A1 | 6/2011 | Hayter | |
| 2011/0256024 A1 | 10/2011 | Cole et al. | |
| 2012/0119902 A1 | 5/2012 | Patro et al. | |
| 2012/0128034 A1 | 5/2012 | Feher | |
| 2012/0191147 A1 | 7/2012 | Rao et al. | |
| 2012/0203076 A1 | 8/2012 | Fatta et al. | |
| 2012/0203306 A1 | 8/2012 | Sarvazyan | |
| 2012/0220351 A1 | 8/2012 | Kerai et al. | |
| 2012/0275319 A1 | 11/2012 | Hennadige et al. | |
| 2013/0018440 A1 | 1/2013 | Chow | |
| 2013/0030494 A1 | 1/2013 | Meredith et al. | |
| 2013/0094601 A1 | 4/2013 | Chang | |
| 2013/0245981 A1 | 9/2013 | Estes et al. | |
| 2014/0064212 A1 | 3/2014 | Ko et al. | |
| 2014/0113590 A1 | 4/2014 | Meylan et al. | |
| 2014/0148868 A1 | 5/2014 | Saba et al. | |
| 2014/0235975 A1 * | 8/2014 | Carnes | G16H 40/67 |
| | | | 600/323 |
| 2014/0323796 A1 | 10/2014 | Medvedev et al. | |
| 2014/0378057 A1 | 12/2014 | Ramon et al. | |
| 2015/0065047 A1 | 3/2015 | Wu et al. | |
| 2015/0077244 A1 | 3/2015 | Lyman et al. | |
| 2015/0341785 A1 | 11/2015 | Young et al. | |
| 2016/0015286 A1 * | 1/2016 | Gitlin | A61N 1/36514 |
| | | | 600/512 |
| 2016/0192867 A1 * | 7/2016 | Esenaliev | A61B 8/5223 |
| | | | 600/316 |
| 2016/0279432 A1 | 9/2016 | Chappel | |
| 2016/0328531 A1 | 11/2016 | DeCondo, Jr. | |
| 2017/0164878 A1 * | 6/2017 | Connor | G09B 19/00 |
| 2017/0185284 A1 | 6/2017 | Bhavaraju et al. | |
| 2017/0222847 A1 | 8/2017 | Feher | |
| 2018/0027077 A1 | 1/2018 | Melodia et al. | |
| 2018/0036547 A1 | 2/2018 | Reddy | |
| 2019/0007817 A1 | 1/2019 | Liu et al. | |
| 2019/0015669 A1 | 1/2019 | Muessig et al. | |
| 2019/0142313 A1 * | 5/2019 | Abou Ismail | A61B 5/0022 |
| | | | 600/316 |
| 2019/0199562 A1 | 6/2019 | Feher | |
| 2019/0357283 A1 | 11/2019 | Liu | |
| 2020/0044844 A1 | 2/2020 | Sridhara et al. | |
| 2020/0060558 A1 | 2/2020 | Aleksov et al. | |
| 2020/0069938 A1 | 3/2020 | Sinnott | |
| 2021/0020294 A1 | 1/2021 | Bharmi et al. | |
| 2023/0053188 A1 * | 2/2023 | Grinberg | A61N 1/36542 |

OTHER PUBLICATIONS

U.S. Appl. No. 17/085,017, filed Oct. 30, 2020.
Baj-Rossi et al. "Fabrication and Packaging of a Fully Implantable Biosensor Array," IEEE, pp. 166-169 (2013).
Extended European Search Report for corresponding EP Application No. 21179178.5-1122 dated Dec. 16, 2021.

* cited by examiner

METHOD FOR MANAGING A PHYSICAL LAYER UTILIZED DURING A WIRELESS CONNECTION WITH MEDICAL DEVICES

CROSS-REFERENCE TO RELATED APPLICATIONS

This application is a continuation-in-part under 35 U.S.C. § 120 of U.S. patent application Ser. No. 17/085,017, filed Oct. 30, 2020, which is incorporated herein by reference.

FIELD

Embodiments of the present disclosure generally relate to techniques for managing wireless communication between medical devices, and more particularly to the utilization of various physical layers during wireless communication between small-format devices such as implantable medical devices or devices in an in vivo analyte monitoring system.

BACKGROUND

An implantable medical device (IMD) is a medical device that is configured to be implanted within a patient anatomy and commonly employs one or more electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external device as well as control patient therapy. The IMD is completely enclosed within the human body. Thus, there is no means of direct interaction with many types of IMDs, other than through wireless communication.

The frequent monitoring and management of analyte levels, such as glucose, ketones, lactate, oxygen, hemoglobin A1C, or the like, can improve the overall health of people and, in particular, people with diabetes. As an example, diabetics are generally required to monitor their glucose levels to ensure that they are being maintained within a clinically safe range, and can also use this information to determine when insulin is needed to manage glucose levels in their bodies or when glucose is needed to raise the level of glucose in their bodies. Clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device can be worn on the body of an individual who requires analyte monitoring. To increase comfort and convenience for the individual, the sensor control device can have a small form-factor, and can be assembled and applied by the individual with a sensor applicator. The application process includes inserting a sensor, such as an in vivo sensor that senses a user's analyte level in a bodily fluid located in the dermal layer of the human body, using an applicator or insertion mechanism, such that the sensor comes into contact with a bodily fluid. The sensor control device can also be configured to transmit analyte data to one or more data receiving devices, from which the individual, her health care provider ("HCP"), or others can review the data and make therapy decisions.

In vivo analyte monitoring systems can be broadly classified based on the manner in which data is communicated between the reader device and the sensor control device. One type of in vivo system is a "Continuous Analyte Monitoring" system, where data can be wirelessly broadcast from the sensor control device to a data receiving device continuously without prompting, e.g., in an automatic fashion according to a broadcast schedule. Another type of in vivo system is a "Flash Analyte Monitoring" system, where data can be wirelessly transferred from the sensor control device in response to a scan or request for data by the data receiving device, such as with a Near Field Communication (NFC) or Radio Frequency Identification (RFID) protocol. A data receiving device can include a variety of hardware components to enable the processing of analyte data received from the sensor control device, and must include telecommunications components to enable the communication with the sensor control device.

However, small-format medical devices, such as IMDs or sensor control devices are typically built with non-replaceable batteries that limit options for communications solutions. Typically, wireless communication is maintained utilizing a low range, low power communications platform. Existing communication solutions experience certain limitations regarding data transmission efficiency and rate. One standard wireless communication platform is Bluetooth Low Energy (BLE). Currently, BLE-enabled sensor control devices use a static Bluetooth physical layer (PHY) and data rate during BLE communication irrespective of the type of transmission or how much data is being transferred. The standard settings are PHY=LE 1M with a data rate of 1 Mb/s. Using a common standard data rate for all transmissions throughout the life of a medical device such as a sensor control device is inefficient given that, for at least a portion of the time, the device is sending or receiving small amounts of data such as alerts and commands. Further, certain types of medical devices, such as the described sensor control devices, are more likely to send/receive alerts, commands, or other smaller data sets. Larger data transfers happen infrequently. The foregoing are only a few examples of why different types of communications sessions are better suited to utilize different data rates and error correction schemes.

An ongoing demand exists to reduce power usage by medical devices such as sensor control devices and implantable medical devices. By limiting power usage, are able to last longer and be constructed with a smaller, less-expensive form factor. One major source of power usage is the aforementioned wireless communication. Reducing the power usage for transmitting and receiving data conflicts with a separate demand for acceptable BLE communication distance. Creating and maintaining a strong BLE connection at an acceptable distance requires significant power consumption by the BLE transceiver.

Previously, it has been proposed to reduce power demand through defining an advertising schedule that uses different transmit power schemes. As an example, in accordance with at least one solution, methods and systems have been proposed that save power usage by defining an advertising schedule that includes a first transmit power setting when an external device (ED), communicating with an implantable medical device (IMD), is in close proximity and a second transmit power setting when the ED is at a further distance. With the advancement of Bluetooth technology to the Bluetooth 5.0 standard, new opportunities are available for improving receiver sensitivity in order to conserve power consumption while at the same time optimizing communication distance.

BRIEF SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the drawings.

In accordance with aspects herein, methods and devices are described to adaptively change transmission data rates and physical layers (PHY) to improve current consumption and/or RF performance. Using other PHYs can give advantages such as higher data rates or forward error correction (FEC) coding. Using lower data rates increases the ability of a sensor control device and a data receiving device to correctly receive each other's signal (reflecting improved receiver sensitivity) which effectively increases the communication range. Increasing receiver sensitivity also means the corresponding transmit power levels can be decreased which saves power.

In accordance with new and unique aspects herein, methods and devices are described that use a lowest data rate for lower payload transmissions such as alerts and commands. This in turn creates a stronger communications connection so that either (1) the communication distance can be extended or (2) for the same communication distance, the transmit power can be reduced to save battery life. When larger data transfers, such as required to backfill analyte data values that could not be transmitted due to a communication gap or firmware updates, are needed, the BLE radios of the sensor control device and data receiving device can switch to a higher data rate until the transfers and updates are complete. In addition to switching data rates, the methods and devices herein switch physical layers to provide additional benefits on top of the data rates.

In accordance with embodiments herein, a medical device is provided. The medical device includes one or more processors. The medical device includes one or more sensors configured to generate signals corresponding to one or more physiological signals detected in a body of a user. The medical device includes a communication module including a transceiver configured to communicate wirelessly with a receiving device using a communication protocol capable of data transmission or reception at multiple data rates. The medical device includes one or more memories communicatively coupled with the one or more processors, the one or more sensors, and the communication module. The one or more memories include instructions to cause the one or more processors to transmit information to the receiving device indicating that the communication module is configured to communicate using the multiple data rates; determine one of multiple data rates to be utilized for at least one of data transmission or reception during a communication session with the receiving device; initialize the communication session with the receiving device using the determined data rate; and transmit, via the communication module to the receiving device and using the determined data rate, communications based on the signals corresponding to the physiological signals.

Optionally, the instructions further cause the one or more processors to transmit a communications packet that represents at least one of an advertisement packet, a scan request packet, or a scan response packet, wherein the communications packet comprises the information indicating that the communication module is configured to communicate using the multiple data rates. Optionally, the communication module is configured to receive a communications packet from the receiving device, the communications packet including an instruction designating the one of the data rates to be used during the communication session. Optionally, the instructions further cause the one or more processors to determine the type of the communications to be transmitted to the receiving device or determine a size of a data set to be transmitted to the receiving device and determine the one of the data rates to be used during the communication session based on at least one of the type of communications or the size of the data set.

Optionally, the communication protocol is further capable of data transmission or reception at the multiple data rates through the use of multiple physical layers. Optionally, each data rate corresponds to a physical layer of the multiple physical layers. Optionally, a first physical layer of the multiple physical layers used by the communication protocol is a backwards-compatible physical layer, a second physical layer is a high data rate physical layer, and a third physical layer supports communication error correction. Optionally, the communication protocol corresponds to a Bluetooth-enabled communication protocol, wherein the communication protocol is Bluetooth version 5.0 or higher. Optionally, a first physical layer corresponds to a LE 1M physical layer, a second physical layer corresponds to a LE 2M physical layer, and a third physical layer corresponds to a LE Coded physical layer.

Optionally, the instructions further cause the one or more processors to receive, via the communication module and from the receiving device, communications using a second data rate of the multiple data rates. Optionally, the instructions further cause the one or more processors to, after transmitting communications to the receiving device based on the signals corresponding to the physiological signals, determine a second of the plurality of data rates to be utilized for at least one of data transmission or reception during the communication session with the receiving device and transmit, via the communication module to the receiving device and using the second determined data rate, communications based on the signals corresponding to the physiological signals. Optionally, the determination of the second of the plurality of data rates is based on monitoring one or more connection criteria of the communication session, the connection criteria comprising a data throughput requirement, a communication type, a battery indicator, a telemetry break condition, or a link condition of the communication session between the medical device and the receiving device.

Optionally, the instructions further cause the one or more processors to determine the one of the plurality of data rates to be utilized for at least one of data transmission or reception during a second communication session with a second receiving device; initialize the second communication session with the second receiving device using the determined data rate, and transmit, via the communication module to the second receiving device and using the determined data rate, communications based on the signals corresponding to the physiological signals. Optionally, the receiving device is a smartphone and the second receiving device is a smartwatch. Optionally, the communication session with the receiving device and the second communication session with the second receiving device are maintained concurrently.

Optionally, the one or more sensors comprise an analyte sensor configured to generate signals corresponding to levels of an analyte in the body of the user. Optionally, the multiple data rates include at least three different data rates. Optionally, the determined data rate is utilized for data transmission during the communication session and a second data rate is utilized for data reception during the communication session.

In accordance with embodiments herein, a method of selecting one of multiple data rates for a wireless communication session between a medical device and a receiving device is provided. The method includes transmitting, by a communication module of the medical device, information to the receiving device indicating that the communication module is configured to communicate using a communication protocol capable of data transmission or reception at the plurality of data rates. The medical device can include one or more sensors configured to generate signals corresponding to one or more physiological signals detected in a body of a user. The method includes determining, by the medical device, one of the plurality of data rates to be utilized for at least one of data transmission or reception during the communication session with the receiving device. The method includes initializing, by the communication module, the communication session with the receiving device using the determined data rate. The method includes transmitting, by the communication module to the receiving device and using the determined data rate, communications based on the signals corresponding to the physiological signals.

In accordance with embodiments herein, one or more computer-readable non-transitory storage media comprising instructions that are operable when executed by a receiving device for communication with a medical device. The instructions are operable to perform a variety of operations. The operations include receiving, by a transceiver of the receiving device, information from the medical device indicating that the medical device is configured to communicate wirelessly using a communication protocol capable of data transmission or reception at multiple data rates. The transceiver of the receiving device is also configured to communicate wirelessly using the communication protocol. The operations include determining one of the multiple data rates to be utilized for data transmission or reception during a communication session with the medical device. The operations include transmitting, by the transceiver of the receiving device and to the medical device, an instruction designating the determined data rate for the communication session. The operations include initializing, via the transceiver, the communication session with the medical device using the determined data rate. The operations include receiving, via the transceiver during the communication session and using the determined data rate, information from the medical device corresponding to one or more physiological signals of a user of the medical device and obtained by the medical device.

In accordance with embodiments herein, an implantable medical device (IMD) is provided. The IMD includes a transceiver configured to communicate wirelessly, with an external device (ED), utilizing a protocol that utilizes multiple physical layers. The transceiver is configured to transmit information indicating that the transceiver is configured with first, second, and third physical layers (PHYs) for wireless communication. The IMD includes memory configured to store program instructions. The IMD includes one or more processors configured to execute instructions to obtain an instruction designating one of the first, second and third PHY to be utilized for at least one of transmission or reception, during a communication session, with the external device and manage the transceiver to utilize, during the communication session, the one of the first, second and third PHY as designated.

Optionally, the transceiver may be configured to transmit a communications packet to represent at least one of an advertisement packet, a scan request packet, or a scan response packet. The communications packet may include the information indicating that the transceiver is configured with the first, second and third PHYs. The transceiver may be configured to receive an ED communications packet from the external device. The ED communications packet may include the instruction designating the one of the first, second and third PHY. The one or more processors may be configured to at least one of 1) determine the type of communication or 2) determine a size of data set to be transferred between the ED and IMD. The one or more processors may be configured to generate the instruction designating the one of the first, second and third PHYs based on at least one of the type of communication or the size of the data set.

Optionally, the protocol may correspond to a Bluetooth protocol. The first, second and third PHY may correspond to LE 1M, LE 2M and LE Coded PHYs, respectively. The instruction may designate the LE 2M PHY when the type of communication corresponds to a large payload communication. The instruction may designate the LE Coded PHY when the type of communication corresponds to a small payload communication. The one or more processors may be configured to manage a receiver of the transceiver to utilize the first PHY in connection with receiving communications packets from the ED and may manage a transmitter of the transceiver to utilize the second PHY in connection with transmitting communications packets to the ED.

In accordance with embodiments herein, an external device (ED) configured to wirelessly communicate with an implantable medical device (IMD) utilizing a protocol that supports multiple physical layers (PHYs) is provided. The ED includes an external transceiver configured to wirelessly communicate with the IMD. The external transceiver is configured to receive a communications packet. The ED includes memory configured to store program instructions. The ED includes one or more processors that are configured, when implementing the program instructions, to analyze the communications packet for information indicating whether the IMD is configured with multiple physical layers (PHYs) for wireless communication, select one of the multiple PHYs based on at least one of a type of communication to occur, or a size of a data set to be transferred, during a communication session and transmit an instruction to the IMD to utilize the one of the multiple PHYs selected for at least one of transmission or reception during the communication session.

Optionally, the one or more processors may be further configured to receive, as the communications packet, an advertisement packet, and analyze a content of the advertisement packet for the information indicating where the IMD is configured with the multiple PHYs. The information analyzed from the communications packet may indicate whether the IMD is compatible with Bluetooth version 5.0 or higher. The one or more processors may be configured to determine the type of communication and select between first or second PHY based on the type of communication. The one or more processors may be configured to determine the size of the data set to be transferred and select between the second PHY or a third PHY based on the size of the data set to be transferred.

Optionally, following the select and transmit operations, the one or more processors may be configured to manage the external transceiver to establish a communication session with the IMD utilizing the one of the multiple PHYs. The one or more processors may be configured to initiate a communication session utilizing a first PHY from the multiple PHY and, to change, during the communication session, to a second PHY from the multiple PHY. The one or more processors may change to the second PHY based on a connection criteria that includes at least one of a data throughput requirement, a communication type, a battery indicator, a telemetry break condition, or link condition of the communications link between the IMD and ED.

In accordance with embodiments herein, a method for managing a wireless communication between an external device (ED) and an implantable medical device (IMD) utilizing a protocol that supports multiple physical layers (PHYs) is provided. The method selects, at one of the ED or IMD, one of multiple PHYs for wireless communication based on a connection criteria. The method transmits an instruction, to another of the ED or IMD, to utilize the one of the multiple PHYs selected for at least one of transmission or reception during the communication session.

Optionally, the method may receive, at the ED, a communications packet from the IMD and may analyze the communications packet for information indicating whether the IMD is configured with multiple physical layers (PHYs) for wireless communication. The ED may perform the selecting the one of the multiple PHYs and transmitting the instruction to the IMD. The method may collect and analyze the connection criteria. The connection criteria may include at least one of a data throughput requirement, a communication type, a battery indicator, a telemetry break condition, or link condition of a communications link between the IMD and ED. The method may determine at least one of 1) a type of communication or 2) a size of the data set to be transferred, and based thereon selecting the one of the multiple PHYs. The method may establish a communication session between the ED and the IMD utilizing the one of the multiple PHYs. The method pay initiate a communication session utilizing a first PHY from the multiple PHY and, changing, during the communication session, to a second PHY from the multiple PHY.

Other systems, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

DETAILED DESCRIPTION

Figure 1:
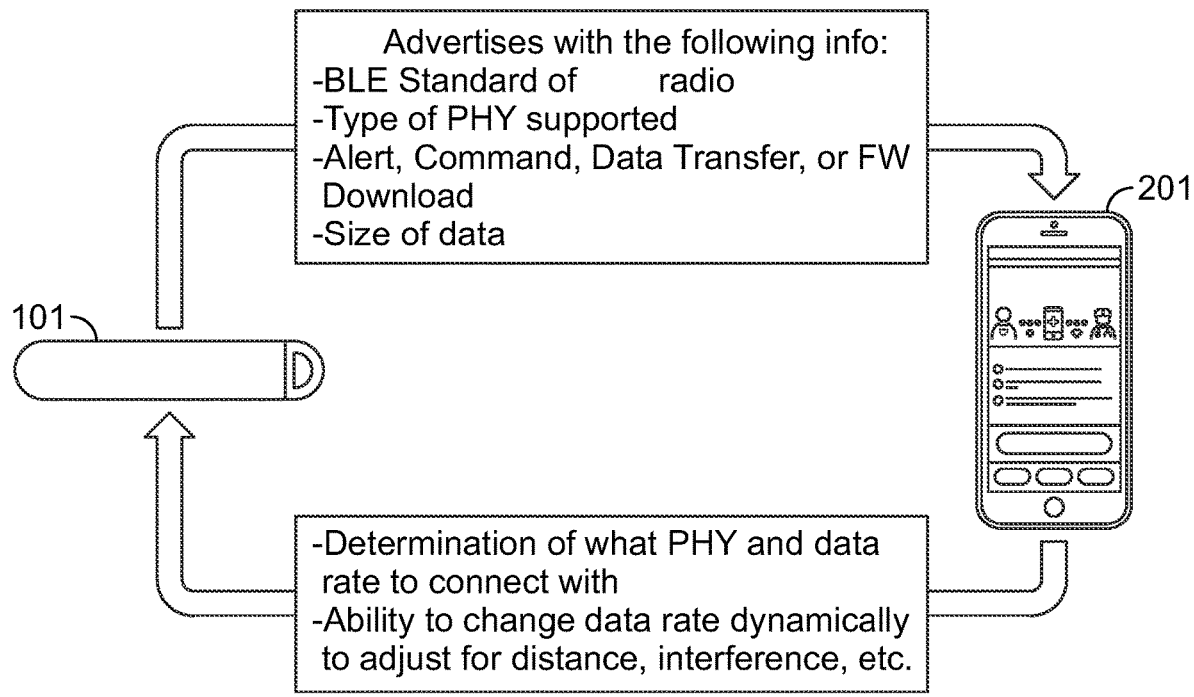
FIG. 1 illustrates a simplified block diagram of a system operated in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

The terms "small", "smaller", "large", and "larger", are used herein in connection with payload to refer to relative size to one another, and not to refer to a specific amount of data. For example, a first payload that is "smaller" as compared to a second payload, simply indicates that the first payload has less data than in the second payload.

The term "actual telemetry break", as used herein, refers to a condition in which a communications link has at least temporarily ended due to one or more of return errors and/or bad packets received by a medical device.

The term "potential telemetry break", as used herein, refers to a condition in which a communications link is maintained, but experiences a number of return errors and/or bad packets received by a medical device in excess of a threshold, thereby indicating a high likelihood that the communications link is about to end.

The term "telemetry break condition", as used herein, refers to a condition of a communications link with respect to an actual or potential telemetry break. A telemetry break condition represents one example of connection criteria.

The terms "low power" and "high power", as used herein, do not refer to absolute power levels, but instead referred to power levels relative to one another.

The term "connection criteria" refers to at least one of data throughput requirement, communication type, a battery indicator, a telemetry break condition or link condition of the communications link between medical devices such as an IMD or sensor control device and ED or data receiving device.

In accordance with new and unique aspects herein, methods and systems have been developed to take advantage of the availability of multiple physical layers (PHYs), such as the additions to the PHYs offered in the Bluetooth 5.0 and higher versions, in connection with improving transmission efficiency, limiting power usage and the like. The PHY represents the bottom layer of the protocol stack. Bluetooth 5.0 and later versions add two new PHY variance (LE 2M and LE coded) as compared to the single PHY variant offered in Bluetooth 4.2 and earlier versions (LE 1M). The LE 2M PHY allows the physical layer to operate at a rate of 2 million symbols per second (2 Ms/s), thereby enabling a higher data rate, as compared to the Bluetooth version 4.2 PHY of LE 1M (having a data rate of 1 million symbols per second). The terms "bits per second", "b/s", "symbols per second", and "s/s", are used interchangeably with one another throughout, although it is recognized that a symbol may not be limited to a single bit, but instead may be defined by a known number of bits. The LE 2M PHY doubles the symbol rate relative to the LE 1M PHY. The LE 1M PHY uses two level Gaussian frequency shift keying (GFSK) with a binary zero represented by a decrease in the carrier frequency by a given frequency deviation (185 kHz) and a binary one represented by increasing the carrier frequency by the same deviation (185 kHz). The LE 2M PHY uses two level GFSK with a binary zero represented by a decrease in the carrier frequency by a given frequency deviation (370 kHz) and a binary one represented by increasing the carrier frequency by the same deviation (370 kHz).

The LE coded PHY allows the communication range to be greatly increased, such as potentially quadrupled, as compared to the range afforded by the LE 1M PHY in accordance with the Bluetooth 4.2 version (all other factors and the environment being equal). The increased range of the LE coded PHY is achieved without increasing the transmission power required, through the use of forward error correction (FEC). However, the added error correction capability afforded in the LE coded PHY sacrifices data rate. More specifically, the LE 1M PHY and LE 2M PHY utilize error detection, such as a cyclic redundancy check (CRC), in which a CRC value is calculated for data packets by the transmitter and appended to the packet. The receiver recalculates the CRC and compares the recalculated value with the value appended to the packet. When the values are not the same, an error is declared. When an error is detected, the receiver requests or "hints" (e.g., by failing to acknowledge receipt of a packet at the link layer) that the transmitter resend the data packet. When a transceiver receives a request for data to be resent, or when a transceiver does not receive an acknowledgment, the transceiver resends the data packet.

The LE coded PHY adds advanced error correction that enables the receiver to not need the data to be retransmitted, but instead allows the receiving device to perform error "correction" (not simply error "detection" as in Bluetooth version 4.2). The forward error correction adds additional redundant bits to transmitted packets, where the redundant bits are intended to support application of the FEC algorithm and to determine the correct value for received bits. By way of example, the FEC encoding may utilize a convolution encoder which generates S-bits for each input bit using a predetermined generator polynomial. Different coding schemes may be utilized, such as a 2-bit (S=2) or an 8-bit (S=8). In a 2-bit encoding scheme, the convolution encoder outputs 2 bits for each single input bit. In an 8-bit encoding scheme, the convolution encoder outputs 8-bits for each single input bit. A pattern mapper converts each bit from the convolution FEC encoder into P symbols where the value of P depends on the coding scheme. When a 2-bit coding scheme is used P=1, when an 8-bit coding scheme is utilized, P=4. The different coding schemes affect transmission range, with the LE Coded 2S scheme PHY having a range that is approximately double the range of the LE 1M PHY, while the range corresponding to the LE coded 8S scheme PHY is approximately four times greater than the range afforded by the LE 1M PHY. However, the data rate associated with the LE coded 8S scheme drops to 125 kb per second (125 Ks/s), and the data rate associated with LE coded 2S scheme drops to 500 kb per second (500 Ks/s), as compared to the 1 Mb per second (1 Ms/s) data rate of the LE 1M PHY.

In accordance with new and unique aspects herein, methods and systems are described in which sending devices and receiving device actively switch to different physical layers (PHY) and corresponding data rates depending upon a type of communication and/or an amount of data to be transferred during the communication session. Embodiments herein seek to maximize the nature of the three different physical layers: LE 1M, LE 2M, and LE Coded. LE 1M is the most common PHY and is compatible with all Bluetooth transceivers. LE 1M can only support the 1 Mb/s data rate and does not support any error corrections. LE 2M can support heavier data transfer loads of 2 Mb/s. LE Coded can support lower data rates such as 125 Kb/s and 500 Kb/s. LE Coded can also use forward error correction to recover erroneous data packets to improve the fidelity of the signal reception. In order to use LE 2M or LE Coded PHYs, both the sending device (e.g., an IMD or sensor control device) and a receiving device (e.g., an ED or data receiving device) must use transceivers that are compliant to the Bluetooth 5.0 standard.

Table 1 below shows a comparison of the effects upon performance when using different PHY and data rates. Performance may be defined in various manners, such as based on bit error rate, signal to noise ratio, dropped connections, number of data packets that are not properly received, and the like. At the lower data rates, when using the LE Coded PHY, significant improvements can be seen regarding communication distance and current savings while maintaining a constant performance. The LE 1M PHY serves as a baseline as it is the current setting for conventional IMDs and sensor control devices. Using a 2 Mb/s data rate will allow larger amounts of data to be transferred faster at the cost of shorter communication range and more power consumption. The lower data rates provide significant improvements in communication distance and power consumption.

TABLE 1

TABLE OF PERFORMANCE VS. DATA RATE AND PHY

| PHY | Data Rate | Loss/Gain (dB) | Distance | Current Consumption |
| --- | --- | --- | --- | --- |
| LE 2M | 2 Mb/s | −3.1 | 0.7 × D | −29% |
| LE 1M | 1 Mb/s | 0 | D | 0% |
| LE Coded 2S | 500 Kb/s | +4.4 | 1.66 × D | 29% |
| LE Coded 8S | 125 Kb/s | +7.0 | 2.24 × D | 40% |

Table 1 illustrates differences in loss/gain (in dB), distance and current consumption in connection with each PHY and data rate relative to reference levels associated with the LE 1M PHY. The loss/gain column represents an amount that the transceiver will need to increase or decrease the gain, relative to a reference level, to afford a same performance level as the reference LE 1M PHY. As shown in Table 1, in order to maintain a same level of performance as the LE 1M PHY, when the PHY is switched to the LE 2M PHY, (e.g., with all other factors remaining equal such as distance, interference, overall environment), the transceiver gain needs to be increased by 3.1 dB. In other words, when a sending device switches from the LE 1M PHY to the LE 2M PHY, the sending device would need to increase the transmit/receive gain by 3.1 dB to maintain a common communication link quality at a given distance D relative to the transmit/receive gain that the transceiver was utilizing when communicating over the LE 1M PHY. The increase of 3.1 dB of gain causes an increase in current consumption by the IMD of approximately 29% as compared to the current consumption of the IMD when utilizing the LE 1M PHY. Note that current consumption is represented as a percent improvement, so a negative percent improvement indicates additional current consumption.

Conversely, when switching from the LE 1M PHY to the LE Coded 2S or LE Coded 8S PHY, if all other factors are maintained constant, the transceiver gain could be decreased by 4.4 dB and 7.0 dB, respectively, (below the gain setting utilized by the LE 1M PHY) to maintain a common communication link quality at a given distance D relative to the transmit/receive gain when communicating utilizing the LE 1M PHY. The decreases of 4.4 dB and 7.0 dB of gain results in lower current consumption by the sending device (when utilizing the LE Coded 2S or LE Coded 8S PHY) of approximately 29% and 40%, respectively, as compared to the current consumption of the sending device when utilizing the LE 1M PHY.

Alternatively, if the sending device (e.g., IMD or sensor control device) maintains the transmit/receive gain/sensitivity constant when switching from the LE 1M to the LE 2M PHY, the sending device will exhibit a same performance, when utilizing the LE 2M PHY at a shorter communications distance, namely at distance of 0.7D relative to the reference distance (D) associated with the LE 1M PHY. Conversely, when switching from the LE 1M PHY to the LE Coded 2S or LE Coded 8S PHY, if all other factors are maintained constant, when the sending device utilizes the LE Coded 2S or LE Coded 8S PHY, the sending device will exhibit a same performance, as when using the LE 1M PHY, at greater communications distances of 1.66D and 2.44D, respectively.

FIG. 1 illustrates a simplified block diagram of a system operated in accordance with embodiments herein. The system includes one or more IMD 101 and one or more external device (ED) 201 (e.g., table computer, smart phone, smart watch, laptop, and/or the like) that are configured to communicate with one another wirelessly over a communications link.

The IMD 101 is implanted within a patient (e.g., proximate to and/or within a heart, proximate to the spinal cord). Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may deliver some type of therapy/treatment, provide mechanical circulatory support and/or merely monitor one or more physiologic characteristics of interest (e.g., PAP, CA signals, impedance, heart sounds).

Additionally or alternatively, the IMD may be any of the implantable devices described in U.S. application Ser. No. 16/930,791, titled "METHODS, DEVICES AND SYSTEMS FOR HOLISTIC INTEGRATED HEALTHCARE PATIENT MANAGEMENT", filed Jul. 16, 2020, which is incorporated by reference in its entirety. As non-limiting examples, the IMD may be a body generated analyte or BGA test device which shall mean any and all equipment, devices, disposable products utilized to collect and analyze a BGA. The terms "body generated analyte" and "BGA" shall have the meaning defines in the U.S. application Ser. No. 16/930,791. The BGA test device may implement one or more of the methods, devices and systems described in the following publications, all of which are incorporated herein by reference in their entireties: U.S. Patent Publication Number 2011/0256024, entitled "MODULAR ANALYTE MONITORING DEVICE", published Oct. 20, 2011; U.S. Patent Publication Number 2010/0198142, entitled "MUL- TIFUNCTION ANALYTE TEST DEVICE AND METHODS THEREFORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,294,404, entitled "REAGENT PACK FOR IMMUNOASSAYS" issued Mar. 15, 1994; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23. 2010; U.S. Pat. No. 7,723,099, entitled "IMMUNOASSAY DEVICE WITH IMMUNO-REFERENCE ELECTRODE" issued May 25, 2010; and Baj-Rossi et al. "FABRICATION AND PACKAGING OF A FULLY IMPLANTABLE BIOSENSOR ARRAY", (2013) IEEE, pages 166-169, all of which are incorporated by reference in their entireties.

For the sake of brevity, the following embodiments will be described in the context of an IMD 101 and ED 201. However, it is recognized that similar procedures can be performed and used by a sensor control device 602 (described, for example, in conjunction with FIG. 7) and data receiving device 620 (described, for example, in conjunction with FIG. 8). In at least one embodiment, the sensor control device 602 can perform the pertinent functions of the IMD 101 with respect to adaptively switching a physical layer and data rate before or during a communication session with a data receiving device 620. Similarly, the data receiving device 620 can perform the pertinent functions of the ED 201.

The determination of which physical layer and data rate to be utilized may be initiated when the transceiver of the medical device (e.g., IMD 101 or sensor control device 602) sends out advertisement packets and/or at any point during a communications session. The advertisement packets may include information such as the BLE Standard (e.g., Bluetooth 4.0, 4.2, 5.0) supported by the device, compatible PHY types (LE 1M, LE 2M, LE Coded), a type of communication to occur (e.g., alert, command, software update, data transfer, etc.), and size of the data to be transferred. When the receiving device, such as an external device 201 (e.g., programmer, bedside monitor, smartphone, etc.) or data receiving device 620 receives the advertisement packet, the device will determine based on the encoded information how best to connect to the medical device. Once the receiving device knows the transceiver capabilities of the medical device, the receiving device can control the transceiver parameters both at the initial connection state and throughout the communication session. The receiving device can control the transceiver capabilities in order to, for example, provide a desired (e.g., optimal) RF performance, battery longevity, expected communication session length, etc. Once a communication session is initiated, the devices are afforded the ability to change the PHY and data rate dynamically to adjust for circumstances such as changes in distance between the communicating devices, changes in orientation of the devices relative to each other or the environment, changes in interference and the like.

Figure 2A:
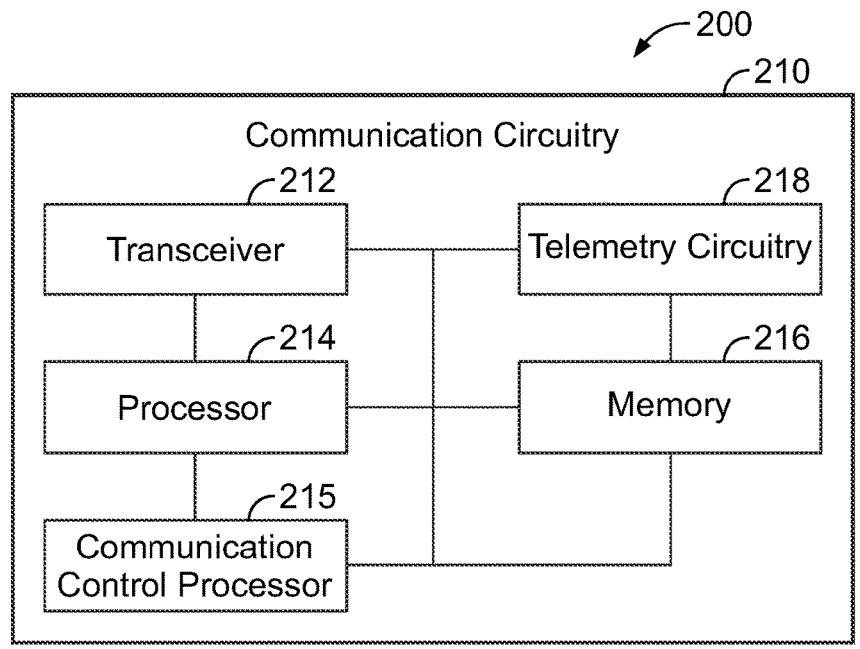
FIG. 2A illustrates a block diagram of communication circuitry utilized in accordance with an embodiments herein.

FIG. 2A illustrates a block diagram of communication circuitry 200 utilized in accordance with an embodiments herein. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

Optionally, the communication circuitry 200 is within an IMD and optionally within one or more external devices. The communication circuitry 200 is configured to establish and maintain the communication link between the IMD 101 and external devices. In one example, the communication circuitry 200 may be configured to handle and/or manage the bi-directional communication link between the IMD 101 and the ED 201. In one example, the communication circuitry 200 is an RF circuit. In another example, the communication circuitry 200 includes a transponder that transmits signals and a receiver that receives signals. In yet another example, the communication circuitry 200 includes a transceiver 212 (T/R) that both transmits signals and receives signals. Specifically, a transceiver includes both a transponder and a receiver. As explained herein, the communication circuitry 200 transmits, among other things, advertisement notices, connection requests, connection responses, scan requests, scan responses, data packets and the like. The transceiver 212 is tuned to communicate with external devices, including the ED 201 over one or more frequency bands and in accordance with a corresponding protocol. The transceiver 212 may include one or more transmitters/transponders, receivers, and/or transceivers. Optionally, the communication circuitry 200 may be electrically coupled to an antenna (not shown). For example, an antenna may be provided within a header of an IMD as one example. As another example, electrodes on or coupled to the IMD may be utilized to convey the wireless communication signals. The communication circuitry 200 also scans for connection request data packets from external devices. In one example the external device is the ED 201 of FIG. 1.

The communication circuitry 200 also includes one or more processors 214 including a communication control processor 215, a local memory 216, and telemetry circuitry 218, all of which may be implemented on a common circuit board, within a common subsystem or within a common integrated circuit. Specifically, the communication circuitry 200 is in communication with other circuits, components, and modules of the IMD 101 including controller circuit, and local memory 216. The communication control processor 215 may support one or more wireless communication protocols while communicating with an external device such as the ED 201, such as Bluetooth low energy, Bluetooth, Medical Implant Communication Service (MICS), and/or the like.

The memory 216 stores instructions implemented by the communication control processor 215. Protocol firmware may be stored in memory 216, which is accessed by the communication control processor 215. The protocol firmware provides the wireless protocol syntax for the communication control processor 215 to assemble data packets, advertisement notices, connection request data packets, connection responses, establish communication links, such as communication, and/or partition data received from an external device, such as ED 201.

The telemetry circuitry 218 in one example monitors the quality of the telemetry or communications link. Alternatively, the telemetry software is stored in the memory that provides instructions that are followed by the communication control processor or one or more of the processors 214 related to the communication circuitry 200. The telemetry circuitry 218 in one example determines when the link, and/or how often the link drops causing interruptions in communications being passed through the communications link. In another example the telemetry circuitry 218 determines the number of return errors received, number of bad packets received, or the like. Optionally, the telemetry circuitry 218 tracks the signal to noise ratio (RSSI) of the communication link. When the communication link is down or not working the telemetry circuitry 218 verifies the power setting of the telemetry link and increases the power setting when a break in the link occurs, or when a link is unable to be established. In this manner, the telemetry circuitry 218 facilitates re-establishment of the link to assist in completing communication sessions. Thus, the telemetry circuitry 218 not only makes determinations regarding when communication breaks occurs including timing to reestablish the link and the like, but additionally, the quality of the telemetry link is determined through various methods including RSSI. The telemetry circuitry 218 also actively corrects any breaks or poor quality communications by increasing power to establish and maintain the link.

Figure 2B:
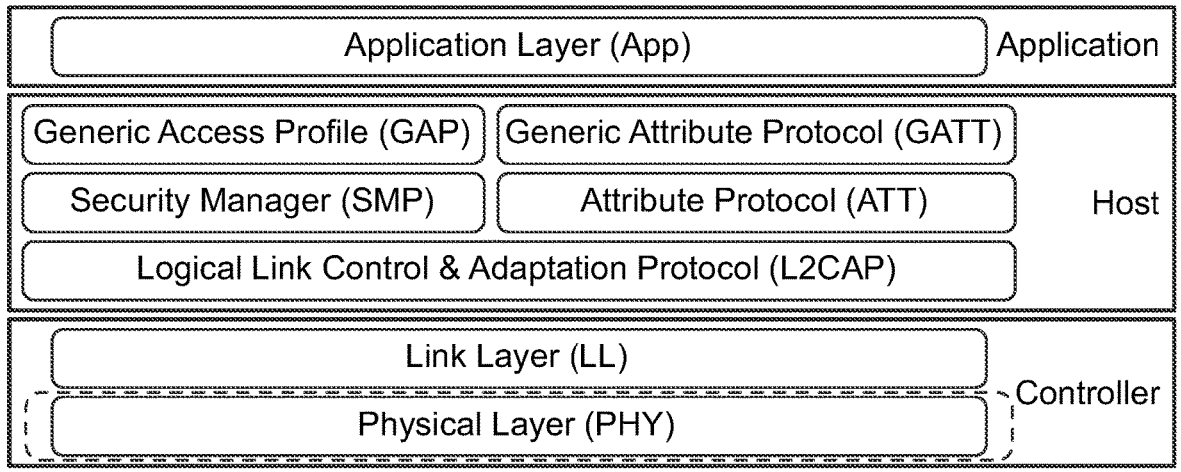
FIG. 2B illustrates a full protocol stack structure of a Bluetooth protocol in accordance with an embodiments herein.

FIG. 2B illustrates a full protocol stack structure of a Bluetooth protocol. The top layer corresponds to various applications that interact with and utilize Bluetooth wireless communication. The host maintains various information, such as the generic access profile (GAP), generic attribute protocol (GATT), secure manager (SMP), attribute protocol (ATT), and logical Link control and adaptation protocol (L2CAP). The controller implements, among other things, the link layer (LL) and the physical layer (PHY).

Returning to FIG. 2A, the communications circuitry 200 is configured to implement the Bluetooth low energy protocol of FIG. 2B, including the multiple physical layers discussed herein. As explained herein, the communications circuitry 200 is configured to support bidirectional communications utilizing a selected one of the LE 1M, LE 2M, LE Coded physical layers (including the LE Coded 2S and LE Coded 8S). Optionally, during a communications session, the communications circuitry 200 may transmit utilizing a first PHY and receive utilizing a second PHY. For example, during a communications session in which the host device (e.g., IME 101 or sensor control device 602) is downloading a new firmware version, the host device may receive data utilizing the LE 2M PHY, while utilizing one of the LE Coded PHY to transmit to the other device (e.g., ED 201 or data receiving device 620). As another example, during a communication session in which the host device is uploading stored data such as EGM signals or analyte level values, the host device may utilize the LE 2M PHY to transmit the stored data to the other device, but utilize one of the LE Coded PHY to receive commands from the other device.

As explained herein, the communications circuitry 200 is configured to communicate wirelessly, with another device, utilizing a protocol that utilizes multiple physical layers. The communications circuitry 200 is configured to transmit information indicating that the transceiver is configured with, for example, first, second and third physical layers (PHYs) for wireless communication. The IMD further comprises memory 216 configured to store program instructions and one or more processors 214 configured to execute instructions to: obtain an instruction designating one of the first, second and third PHY to be utilized for at least one of transmission or reception, during a communication session, with the external device; and manage the transceiver 212 to utilize, during the communication session, the one of the first, second and third PHY as designated.

For example, the transceiver 212 is configured to transmit a communications packet representing at least one of an advertisement packet, a scan request packet, or a scan response packet, the communications packet including the information indicating that the transceiver is configured with the first, second and third PHYs. Additionally or alternatively, the transceiver 212 is configured to receive a communications packet from the external device, the communications packet including the instruction designating the one of the first, second and third PHY. Additionally or alternatively, the one or more processors 214 are configured to at least one of 1) determine the type of communication or 2) determine a size of data set (also referred to as a data throughput requirement) to be transferred between the devices, the one or more processors 214 configured to generate the instruction designating the one of the first, second and third PHYs based on at least one of the type of communication or the size of the data set.

In accordance with embodiments herein, when the protocol corresponds to a Bluetooth protocol, the first, second and third PHY corresponding to LE 1M, LE 2M and LE Coded PHYs, respectively, and the instruction designates the LE 2M PHY when the type of communication corresponds to a large payload communication. The instruction designates the LE Coded PHY when the type of communication corresponds to a small payload communication. The one or more processors are configured to manage a receiver of the transceiver to utilize the first PHY in connection with receiving communications packets and to manage a transmitter of the transceiver to utilize the second PHY in connection with transmitting communications packets.

In accordance with embodiments herein, the other device (e.g., ED 201 or data receiving device 620) is also configured to wirelessly communicate with the host device utilizing a protocol that supports multiple physical layers (PHYs). The other device can comprise an external transceiver configured to wirelessly communicate with the host device; the external transceiver configured to receive a communications packet; memory configured to store program instructions; and one or more processors that are configured, when implementing the program instructions, to: analyze the communications packet for information indicating whether the IMD is configured with multiple physical layers (PHYs) for wireless communication; select one of the multiple PHYs based on at least one of a type of communication to occur, or a size of a data set to be transferred, during the communication session; and transmit an instruction to the IMD to utilize the one of the multiple PHYs selected for at least one of transmission or reception during the communication session.

Additionally or alternatively, the one or more processors are further configured to receive, as the communications packet, an advertisement packet, and analyze a content of the advertisement packet for the information indicating where the sending device is configured with the multiple PHYs. Additionally or alternatively, the information analyzed from the communications packet indicates whether the device is compatible with Bluetooth version 5.0 or higher. Additionally or alternatively, the one or more processors are configured to determine the type of communication and select between first or second PHY based on the type of communication. Additionally or alternatively, the one or more processors are configured to determine the size of the data set to be transferred and select between the second PHY or a third PHY based on the size of the data set to be transferred. Additionally or alternatively, following the select and transmit operations, the one or more processors are configured to manage the device transceiver to establish a communication session utilizing the one of the multiple PHYs.

Figure 3:
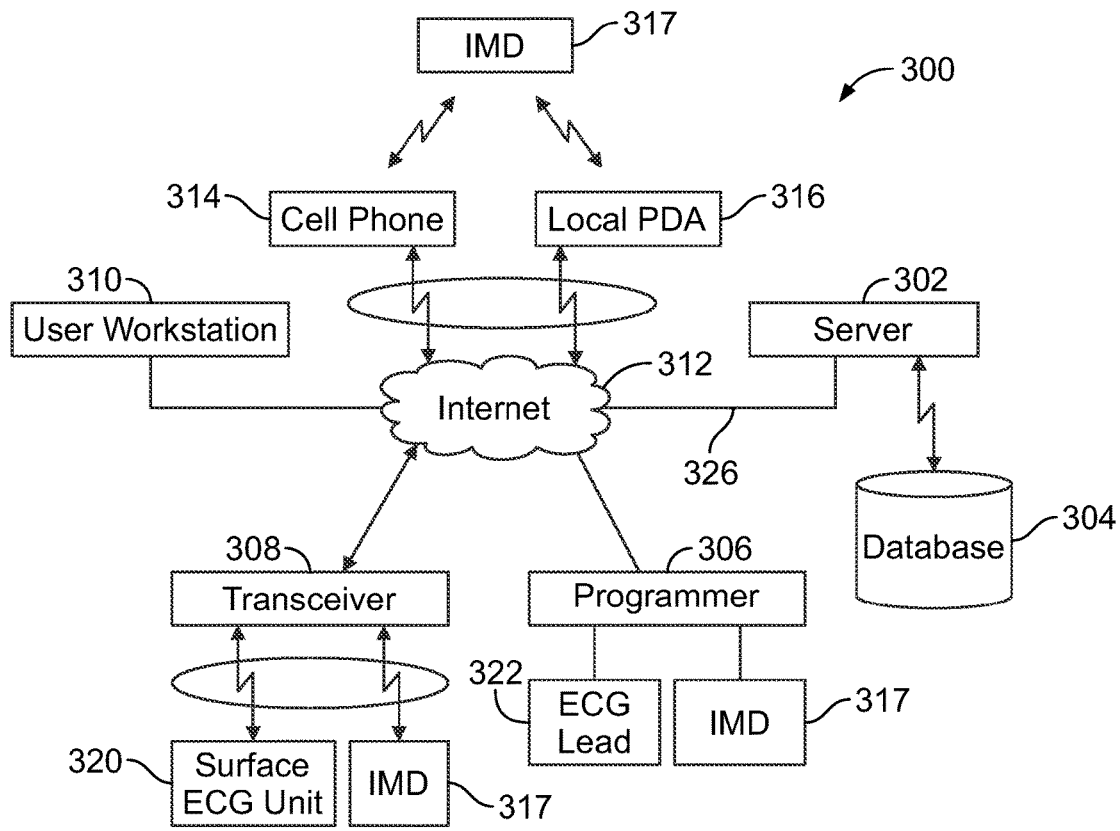
FIG. 3 illustrates a distributed processing system in accordance with one embodiment.

FIG. 3 illustrates a distributed processing system 300 in accordance with one embodiment. In one example, the distributed processing system 300 includes and implements the communication circuitry 200 as provided in FIG. 2A in one or more of the devices shown in FIG. 3. The distributed processing system 300 includes a server 302 connected to a database 304, a programmer 306, a local RF transceiver 308 and a user workstation 310 electrically connected to a communication system 312. Any of the processor-based components in FIG. 3 (e.g., workstation 310, cell phone 314, PDA 316, server 302, programmer 306, IMD 101) may communicate with an IMD 317 that in one example is IMD 101 of FIG. 1. In one example, the local RF transceiver 308 is the transceiver of 212 of FIG. 2A. The various components illustrated in FIG. 3 are configured to communicate over a common wireless protocol, such as the Bluetooth low energy protocol. The components may implement various versions of the BLE protocol. For example, a subset of the IMDs 317 may implement a version 4.0 or lower version of the BLE protocol (e.g., having only the LE 1M PHY), while another subset of the IMD 317 may implement a version 5.0 or higher version of the BLE protocol (e.g., having multiple PHYs). The cell phone 314 and programmer 306 may include transceivers that support multiple PHYs (e.g., LE 1M, LE2M, LE coded), while the local PDA 316 only supports the LE 1M PHY.

Various components within the system 300 may determine which PHY to utilize during communication, including but not limited to, the IMD 317, cell phone 314, local PDA 316, transceiver 308, programmer 306 and server 302. For example, the programmer 306 and/or cell phone 314 may initially determine which physical layer to utilize during a communication session. Additionally or alternatively, an IMD 317, with which the cell phone 314 and/or programmer 306 communicate, may make the initial determination of the physical layer. Additionally or alternatively, the IMD 317 may determine that the initial physical layer designator for communication is not affording a sufficient level of performance or signal quality and instruct the cell phone 314, programmer 306 or other external device to switch to a more reliable physical layer (e.g., switching from the LE 2M layer to the LE 1M or LE Coded layer).

The communication system 312 may be the internet, a voice over IP (VoIP) gateway, a local plain old telephone service (POTS) such as a public switched telephone network (PSTN), a cellular phone based network, and the like. Alternatively, the communication system 312 may be a local area network (LAN), a campus area network (CAN), a metropolitan area network (MAN), or a wide area network (WAN). The communication system 312 serves to provide a network that facilitates the transfer/receipt of information such as cardiac signal waveforms, ventricular and atrial heart rates.

The server 302 is a computer system that provides services to other computing systems over a computer network. The server 302 interfaces with the communication system 312 to transfer information between the programmer 306, the local RF transceiver 308, the user workstation 310 as well as a cell phone 314, a personal data assistant (PDA) 316, and IMD 317 to the database 304 for storage/retrieval of records of information. On the other hand, the server 302 may upload raw cardiac signals from an implanted lead 322, surface ECG unit 320 or the IMD 317 via the local RF transceiver 308 or the programmer 306.

The database 304 stores information such as cardiac signal waveforms, ventricular and atrial heart rates, thresholds, and the like, for a single or multiple patients. The information is downloaded into the database 304 via the server 302 or, alternatively, the information is uploaded to the server from the database 304. The programmer 306 is similar to an external device or instrument and may reside in a patient's home, a hospital, or a physician's office. The programmer 306 interfaces with the lead 322 and the IMD 317. The programmer 306 may wirelessly communicate with the IMD 317 and utilize protocols, such as Bluetooth, GSM, infrared wireless LANs, HIPERLAN, 3G, satellite, inductive as well as circuit and packet data protocols, and the like. Alternatively, a hard-wired connection may be used to connect the programmer 306 to the IMD 317. The programmer 306 is able to acquire cardiac signals from the surface of a person (e.g., ECGs), intra-cardiac electrogram (e.g., IEGM) signals from the IMD 317, and/or cardiac signal waveforms, ventricular and atrial heart rates, and detection thresholds from the IMD 317. The programmer 306 interfaces with the communication system 312, either via the internet or via POTS, to upload the information acquired from the surface ECG unit 320, the lead 322 or the IMD 317 to the server 302.

The local RF transceiver 308 interfaces with the communication system 312 to transmit and receive telemetry data and information being transmitted to and from the RF transceiver 308. In one example the communication system monitors the communication link and records telemetry breaks, length of breaks, number of breaks in a given interval, time to reestablish a signal, signal to noise ratio, and the like. In this manner the communication system 312 provides with a user the quality and/or strength of a communication signal and amount or strength of local interference. In addition, the communication system 312 (e.g., server 302, cell phone 314, work station 310, programmer 306) may, based on the monitored communication quality, increase or decrease the power of a signal being transmitted. In one example, the communication system 312 monitors both advertising channels and connection channels, thus providing advertising data packets through and communicating through the advertising channels with external devices. Similarly, the communication system 312 is able to provide a communication pathway through a connection channel.

The user workstation 310 may interface with the communication system 312 to download cardiac signal waveforms, ventricular and atrial heart rates, and detection thresholds via the server 302 from the database 304. Alternatively, the user workstation 310 may download raw data from the surface ECG units 320, lead 322 or IMD 317 via either the programmer 306 or the local RF transceiver 308 or cell phone 314 or PDA 316. Once the user workstation 310 has downloaded the cardiac signal waveforms, ventricular and atrial heart rates, or detection thresholds, the user workstation 310 may process the information in accordance with one or more of the operations described above. The user workstation 310 may download the information and notifications to the cell phone 314, the PDA 316, the local RF transceiver 308, the programmer 306, or to the server 302 to be stored on the database 304.

Figure 4:
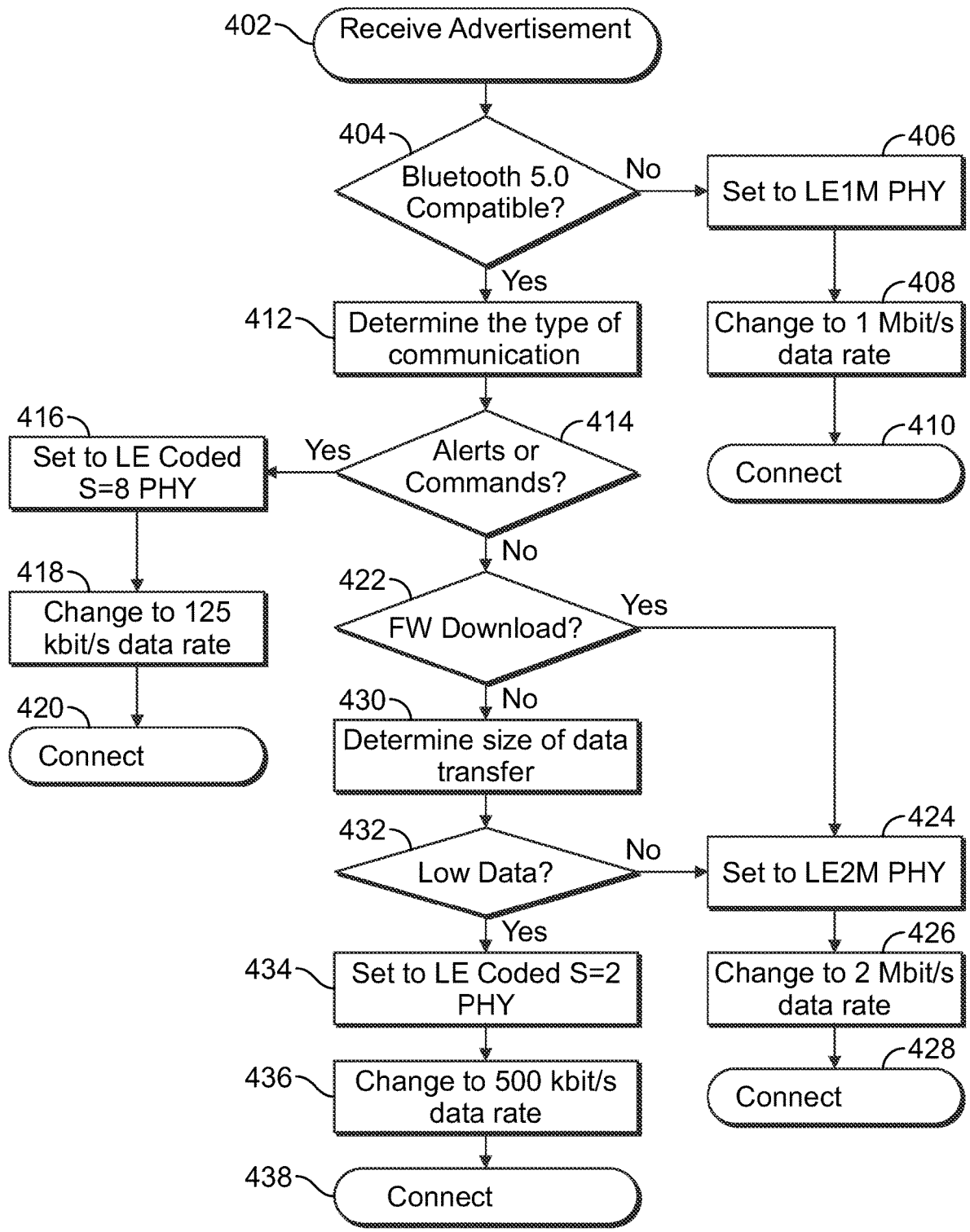
FIG. 4 illustrates a flow block diagram of a method for managing physical layer usage for communication between medical devices in accordance with one embodiment.

FIG. 4 illustrates a flow block diagram of a method for managing physical layer usage for communication between medical devices. In the specific example illustrated by FIG. 4, the medical devices include an external device and an implantable medical device, however, it is recognized that similar methods may be used with other suitably configured medical devices, such as a sensor control device 602 and data receiving device 620 as further described herein. The method may be implemented by hardware components, software components, and/or a combination of hardware components and software components working together to implement the method. The following description will be provided in the context of an external device acting as a host by receiving an advertisement and making the various determinations to select the PHY to be utilized. Although, it is understood that in certain instances, the IMD may serve as the host, and in other instances, a remote server may serve as the host when directly or indirectly communicating with an IMD.

At 402, one or more processors of the host (e.g., external device) receive a communications packet transmitted by the peripheral (e.g., IMD). For example, the communications packet may represent at least one of an advertisement packet, a connect request packet, a connect response packet, a scan request packet, a scan response packet, and the like. The communications packet includes information indicating whether the transceiver of the peripheral is configured with the first, second and third PHYs. Additionally or alternatively, the transceiver is configured to receive an ED communications packet from the host, the ED communications packet including the instruction designating the one of the first, second and third PHY. Additionally or alternatively, the one or more processors are configured to at least one of 1) determine the type of communication or 2) determine a size of data set (data throughput requirement) to be transferred between the ED and IMD, the one or more processors configured to generate the instruction designating the one of the first, second and third PHY's based on at least one of the type of communication or the size of the data set.

At 404, the one or more processors of the host analyze the advertisement notice to determine certain information about the peripheral. Among other things, the host (also referred to as the "master" throughout) determines communications capability information about the IMD, such as which Bluetooth standard is supported by the IMD (e.g., Bluetooth 4.0, 4.2, 5.0), compatible PHY types supported by the IMD (e.g., LE 1M, LE2M, LE coded) and the like. When the IMD is determined to support Bluetooth 5.0 or above versions and/or determined to be compatible with PHY types of LE 2M and LE coded, flow moves to 412. Otherwise, flow moves to 406.

At 406, the one or more processors of the host set the PHY to be utilized during the transmit and receive operations to a first PHY that may represent the only PHY type supported by the peripheral (e.g., the LE 1M PHY). At 408, the transceiver of the host changes to the first PHY level and the corresponding data rate. In the present example, the transceiver switches to maintain a data rate of 1 Mb/s.

At 410, the host and the peripheral exchange additional information to establish a communications session. The operations at 406-410 may be implemented utilizing the PHY Update Procedure, as described in Section 5.1.10 the Bluetooth Specification Version 5.0, volume 6, part B. The version 5.0, volume 6, part B is attached hereto as appendix A, and "capitalize" field names described herein shall have the meanings set forth in the Bluetooth Specification version 5.0, volume 6. The Bluetooth specification Version 5.0, volume 6 is expressly incorporated herein by reference in its entirety. The PHY update procedure may be initiated either upon request by the host or autonomously by the link layer of the peripheral. Either the host or peripheral (e.g., external device or IMD; data receiving device 620 or sensor control device 602) may initiate the PHY update procedure at any time after entering the connection state. The link layer PHY preferences may change during a connection or between connections and therefore, are not necessarily cached by peer devices. When the PHY update procedure is initiated by the host (e.g., external device), the host sends an LL_PHY_REQ PDU (link layer PHY request protocol data unit). The peripheral responds with an LL_PHY_UPDATE_IND PDU (LL PHY update indication PDU).

Alternatively, when the PHY update procedure is initiated by the peripheral, the peripheral sends an LL_PHY_REQ PDU, in response to which the host responds with an LL_PHY_UPDATE_IND PDU. The TX_PHYS (transmit physical later) and RX_PHYS (receive PHY) fields of the LL_PHY_REQ and LL_PHY_RSP PDUs shall be used to indicate the PHYs that the sending link layer prefers to use. If the sender wants a symmetric connection (e.g., one where the two PHYs are the same), the sender should make both fields the same, only specifying a single PHY. The M_TO_S_PHY (Host to peripheral physical layer) and the S_TO_M_PHY (peripheral to host physical layer) fields of the LL_PHY_UPDATE_IND PDU shall indicate the PHYs that should be used after the incident. If the host initiates the PHY update procedure, the host shall determine the PHY to use in each direction based on the contents of the LL_PHY_REQ and LL_PHY_RSP protocol data units (PDUs) using the following rules: 1) the M_TO_S_PHY field of the LL_PHY_UPDATE_IND PDU shall be determined from the host's TX_PHYS field and the peripheral's RX_PHYS field; 2) the S_TO_M_PHY field of the LL_PHY_UPDATE IND PDU shall be determined from the host's RX_PYS field and the peripheral's TX_PHYS field. In each of the foregoing cases, the following rules apply: 1) if, for at least one PHY, the corresponding bit is set to 1 in both the TX_PHYS and RX_PHYS fields, the host shall select any one of those PHYs for that direction; 2) if there is no PHY for which the corresponding bit is set to 1 in both the TX_PHYS and RX_PHYS fields, the host shall not change the PHY for that direction.

If the peripheral initiates the PHY update procedure, the host shall determine the PHY to use in each direction based on the contents of the LL_PHY_REQ PDU sent by the peripheral using the following rules: 1) the RX_PHYS field of the peripheral's PDU; 2) the S_TO_M_PHY field of the LL_PHY_UPDATE_IND PDU shall be determined from the TX_PHYS field of the peripheral's PDU. In each of the foregoing cases the following rules apply: 1) if, for at least one PHY, the PHY is one that the host prefers to use and the corresponding bit is set to 1 in the relevant field of the peripheral's PDU, the host shall select any one of those PHYs for that direction; 2) if there is no PHY which the host prefers to use and for which the corresponding bit is set to 1 in the relevant field of the peripheral's PDU, the host shall not change the PHY for that direction.

The following discussion shall apply irrespective of which device initiated the PHY update procedure. Irrespective of the above rules, the host may leave both directions unchanged. If the peripheral specified a single PHY in both the TX_PHYS and RX_PHYS fields and both fields are the same, the host shall either select the PHY specified by the peripheral for both directions or shall leave both directions unchanged. Both devices shall use the new PHYs starting at the instant. If a host or peripheral sends an LL_PHY_REQ PDU to a device that does not understand that PDU, then the receiving device shall send an LL_UNKNOWN_RSP PDU in response. The procedure has completed when: 1) an LL_UNKNOWN_RSP or LL_REJECT_EXT_IND PDU has been sent or received; 2) an LL_PHY_UPDATE_IND PDU indicating that neither PHY will change has been sent or received; or 3) the host sends an LL_PHY_UPDATE_IND PDU indicating that at least one PHY will change and the instant has been reached. In this case, the procedure response timeout shall be stopped on the host when it sends that PDU and on the peripheral when it receives that PDU. The controller shall notify the host of the PHYs now in effect when the PHY Update Procedure completes if either it has resulted in a change of one or both PHYs or if the procedure was initiated by a request from the Host. Otherwise, it shall not notify the host that the procedure took place.

Returning to 404, when flow moves to 412, the one or more processors of the host determine the type of communication to occur. Nonlimiting examples of communication types may include alert communications, command communications, software updates, data transfers and the like. Alert and command type communications include relatively small amounts of information, also referred to as a small or smaller payload communications, such as when an IMD is conveying an alert to an external device or when an external device may be downloading a command to direct the IMD to change an operation (e.g., switch to a different pacing mode, change one or more pacing parameters and the like). Software update communications include a relatively large amount of information, also referred to as large or larger payload communications, that is downloaded to the IMD. For example, a software update (including firmware updates) may modify, add, or replace a therapy algorithm, detection algorithm, and the like. The large payload communications may also include data transfers, such as when uploading large amounts of data from the IMD to the external device. For example, a data transfer may involve transfer of data, such as EGM signals, stored over a period of time, along with data markers and other analytics identified by the IMD.

At 414, the one or more processors of the host determine whether the current communication type represents a small payload (e.g., an alert or command type communication) and if so, flow moves to 416. Otherwise, flow moves to 422.

At 416, the one or more processors of the host set the PHY to be utilized during the transmit and receive operations to a second PHY that is deemed well-suited for the alert/command type communications. In the present example, the second PHY is set to correspond to the LE coded PHY and is set with S=8. At 418, the transceiver of the host changes to the second PHY and the corresponding data rate. In the present example, the transceiver switches to maintain a data rate of 125 Kb/s at the LE coded S8 PHY.

At 420, the host and the peripheral exchange additional information to establish a communications session. The operations at 416-420 may include the exchange of the various PDU discussed above in connection with setting the PHY at 406, changing the data rate at 408 and establishing a connection at 410.

Returning to 414, when flow moves to 422, the one or processors of the host determine whether the type of communication corresponds to a software update, such as a firmware download. When the communication corresponds to a software update, flow branches to 424. Otherwise, flow continues to 430.

At 424, the one or more processors of the host set the PHY to be utilized during the transmit and receive operations to a third PHY that is deemed well-suited for the software update type communications. In the present example, the third PHY is set to correspond to the LE 2M PHY. At 426, the transceiver of the host changes to the third PHY and the corresponding data rate. In the present example, the transceiver switches to maintain a data rate of 2 Mb/s at the LE 2M PHY. At 428, the host and the peripheral exchange additional information to establish a communications session. The operations at 424-428 may include the exchange of the various PDU discussed above in connection with setting the PHY at 406, changing the data rate at 408 and establishing a connection at 410.

Returning to 422, when the flow moves to 430, the process has determined that the communication does not relate to an alert or command, nor a software update. Accordingly, the one or more processors of the host determine the size of a data transfer to occur during the communication.

At 432, the one or more processors of the host determine whether the size of the data transfer exceeds or falls below a threshold, and based thereon flow branches to 424 or 434. For example, the communication may correspond to uploading ECG signals (saved in the IMD) in combination with event markers and other analytics determined by the IMD or otherwise backfilling data stored by the peripheral and not yet uploaded to the other device. When ECG signals and related markers/analytics are to be uploaded, the size of the data transfer is considered to be relatively large, and would exceed the threshold at 432, thereby directing flow to 424. As noted above, at 424, the one or more processors utilize the LE 2M PHY and the data rate of 2 Mb per second. Alternatively, the size of the data transfer may be much smaller, such as when limited results of ECG analysis are to be uploaded. For example, an IMD may simply upload a level of burden associated with an arrhythmia of interest, a battery level, and the like. When a smaller amount of data is to be transmitted, flow moves from 432 to 434. At 434, the one or more processors of the host set the PHY to the third PHY, but set the encoding to a different encoding level, such as the LE coded PHY while utilizing S2 encoding. At 436, the transceiver of the host changes to the third PHY level and the corresponding data rate. In the present example the transceiver switches to maintain a data rate of 500 Kb/s. At 438, the host and the peripheral exchange additional information to establish a communication session. The operations at 434-438 may include the exchange of the various PDU discussed above in connection with setting the PHY at 406, changing the data rate at 408 and establishing a connection at 410.

As explained in accordance with the process of FIG. 4, when the external device (e.g., programmer) first detects an advertisement notice from the IMD, the external device determines what version of the Bluetooth wireless communication standard is implemented by the IMD. If the IMD uses a transceiver configured in accordance with a Bluetooth standard less than 5.0, then the external device will establish a communication session with the IMD utilizing the single PHY associated with older Bluetooth standards, namely the LE 1M PHY (as that is the only PHY supported by the IMD). The LE 1M PHY only supports a 1 Mb/s data rate for connection. If, however, the IMD includes a transceiver configured to utilize a Bluetooth 5.0 or above standard, then the next step is to determine the purpose of the communication session. If an alert message needs to be sent from the IMD to the external device or a command needs to be sent from the external device to the IMD, the lowest data rate can be applied as this type of transaction is not data heavy. The external device will connect using the LE Coded 8S PHY with the data rate set to 125 Kb/s. If a more substantial transmission such as a firmware download or data transfer was needed, then the programmer would need to identify whether a low data rate or high data rate should be used. For a firmware download and a large data transfer, the highest data rate would be used. The external device would connect using LE 2M PHY with 2 Mb/s data rate. Alternatively, if the amount of data transferred is relatively low, then a lower data rate of 500 Kb/s with an LE Coded 2S PHY can be used.

It should be recognized that while the flowchart in FIG. 4 illustrates what an initial connection might look like, this process also allows for the host to dynamically change the PHY and data rate settings dynamically during a communication session. For example, the decisions and branches of FIG. 4 may be applied during a communication session. If the data payload is heavier than expected, the programmer can switch to a higher data rate to speed up the data transfer. Alternatively, if the communication session is suffering from interference or loss of connection, the programmer can switch to a lower data rate to strengthen the connection at the cost of longer session duration. Lastly, if battery capacity is a constraint, lower data rates can be used to save on current consumption.

Figure 5:
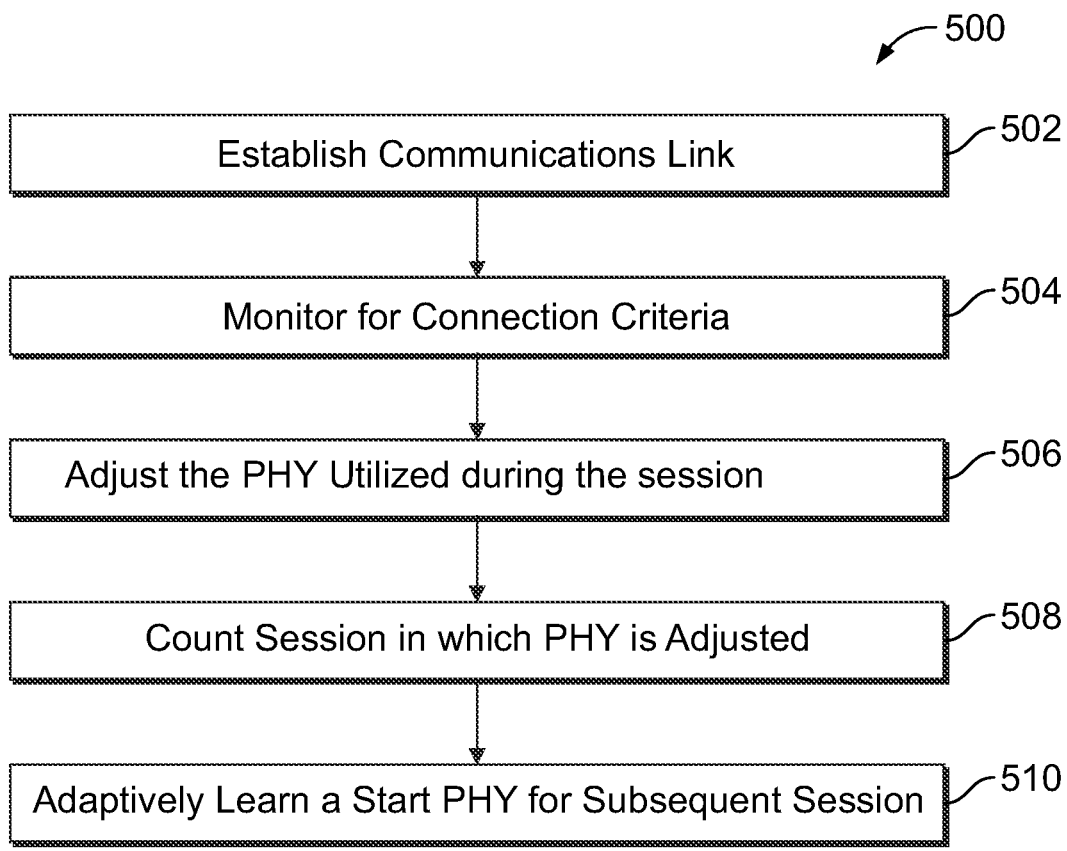
FIG. 5 thus illustrates a flow block diagram of a method for managing selection of the physical layer during a communication session between medical devices in accordance with one embodiment.

FIG. 5 thus illustrates a flow block diagram of an alternative method for managing change of the physical layer during a communication session between medical devices. The method may be implemented by hardware components, software components, and/or a combination of hardware components and software components working together to implement the method. In the specific example illustrated by FIG. 5, the medical devices include an external device and an implantable medical device, however, it is recognized that similar methods may be used with other suitably configured medical devices, such as a sensor control device 602 and data receiving device 620 as further described herein.

At 502, one or more processors of the host device (e.g., ED or data receiving device 620) and peripheral device (e.g., IMD or sensor control device 602) establish a communications link, utilizing a desired physical layer that may be chosen in various manners. For example, the initial physical layer or combination of layers may be chosen in accordance with the process of FIG. 4. Alternatively, the initial physical layer may be predetermined based on prior communication sessions. For example, the external device and IMD may be preprogrammed to begin all communication sessions with the physical layer available in the Bluetooth standard version 4.0 (e.g., LE 1M PHY).

At 504, one or more processors monitor connection criteria during the current session, such as one or more of telemetry break condition, a data throughput requirement, a battery indicator, a communication type or a link condition. In one example, the connection criteria correspond to a telemetry break condition that is an actual break where communication is lost for a predetermined interval and must be restored or reestablished. The predetermined interval may be a second, less than a second, more than a minute, and the like. In another example, the telemetry break condition is a potential telemetry break. The potential telemetry break is determined based on measured parameters such as signal strength, interference noise level, signal to noise ratio, and the like. In one example a threshold is provided related to one of these parameters, such as signal to noise ratio, that once exceeded, or once falling below the threshold indicates the potential telemetry break is presented. In one example monitoring the telemetry break condition includes determining a number of return errors from sent data packets. In another example, monitoring includes determining the number of bad packets received by the one or more of the devices in the communication session. As another example, the connection criteria may include a change in the type of communication, such as a transition from a low/small payload communication (e.g., an alert or command) to a high/large payload communication (e.g., transferring EGM data from the IMD to the external device). As another example, the connection criteria may include a change from a larger payload communication to a smaller payload communication. For example, a communication session may begin by downloading a software change, firmware update or other higher payload communication, in connection with which a higher data rate physical layer (e.g., LE 2M) may be used. Once the software change or firmware update is completed it may be desirable to continue a communication session but with a low/small payload communication, such as to confirm the operation of the software change or firmware update. When switching to a lower payload communication, the PHY may switch to the LE Coded 2S or 8S PHY (e.g., while a series of tests are implemented to confirm the operation of the software change or firmware update, in which commands are sent from the external device to the IMD and responses are returned).

At 506, one or more processors adjust the PHY utilized by the devices between small and large payload PHY, during the current session based on the connection criteria. In one example the PHY is changed when a pre-existing condition occurs, such as to increase the data rate from a higher data rate to a lower data rate during a current session in response to a telemetry break, and increase the demand and data throughput or another change in connection criteria. Alternatively, the PHY may be changed from a lower data rate to a higher data rate during a current session when the signal to noise ratio rises above a threshold level during a current session, or a change in the data throughput increases.

At 508, one or more processors increments a count of a number of communications sessions that utilized the current PHY(s). In one example, when the one or more processors determine an in-session PHY transition occurs from the higher data rate to a lower data rate, and in response thereto, the one or more processors increment the count of the number of sessions in which the devices utilized the LE 1M or LE Coded PHY that support lower data rates. The increment can be represented by a numerical value, such as one, another numerical value, or the like. The one or more processors optionally can determine if the count of the number of sessions in which the IMD utilized the lower data rate has reached a threshold value; and in response to reaching the threshold value, defined the starting PHY for the next communication session to correspond to the PHY that supports the lower data rate (e.g., starting with the LE coded 2S PHY). Different measured events may result in the same result to the count, such as adding one to a count, or may result in a different result to the count.

At 510, the one or more processors adaptively learn a PHY level to be utilized to initiate a next session or certain types of sessions following the current session based on the counting of the number of sessions. In one example, the one or more processors keep track of the count at 508 and when the count reaches a threshold level, then when a next session begins the one or more processors automatically provide a lower data rate PHY to start the next session. Optionally, when a non-telemetry break condition includes determining no return errors or bad packets were received by a device during the session, the count may be decremented. In yet another example, multiple iterations of counts can occur. Specifically, a first count may provide the amount of times a telemetry break or other connection criteria occurs during sessions while a second count may provide the amount of times a signal to noise ratio or other connection criteria is below a threshold. By keeping track of the count of predetermined events that indicate the interference level in a known environment, the one or more processors are able to adaptively determine the start PHY for a given environment and given data demand while keeping power usage low for other environments and uses. Thus, the power usage (e.g., associated with the LE 2M PHY) does not need to remain elevated at times when the elevated power level is unneeded (e.g., associated with the LE 1M PHY). Consequently, power is saved, increasing battery life.

While the foregoing embodiments are described in connection with IMDs and EDs, as further described herein, it is recognized that the techniques associated therewith, and particularly as relating to various communications protocols, may be implemented by, for, or in connection with other medical devices, particularly small-format medical devices such as sensor control devices and data receiving devices that can be associated with an analyte monitoring system as described herein.

Generally, embodiments of the present disclosure include systems, devices, and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. The embodiments provided herein are improvements to reduce the likelihood that a sensor is improperly inserted or damaged, or elicits an adverse physiological response. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

Furthermore, the systems and methods presented herein can be used for operations of a sensor used in an analyte monitoring system, such as but not limited to wellness, fitness, dietary, research, information or any purposes involving analyte sensing over time. As used herein, "sensor" can refer to any device capable of receiving sensor information from a user, including for purpose of illustration but not limited to, body temperature sensors, blood pressure sensors, pulse or heart-rate sensors, glucose level sensors, analyte sensors, physical activity sensors, body movement sensors, or any other sensors for collecting physical or biological information. Analytes measured by the analyte sensors can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Figure 6A:
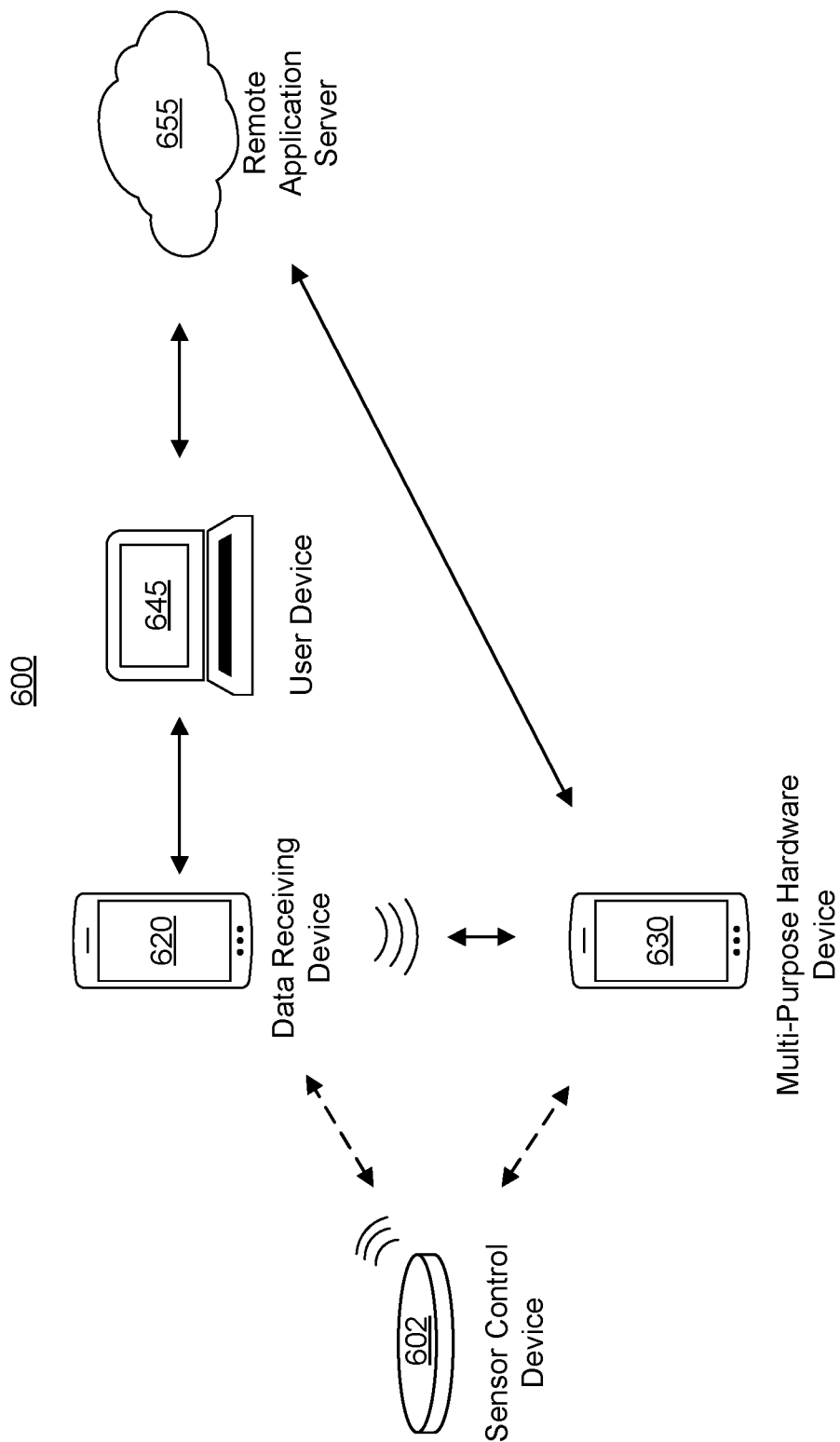
FIGS. 6A-6B are diagrams illustrating operating environments of an example analyte monitoring system for use with the techniques described herein.
Figure 6B:
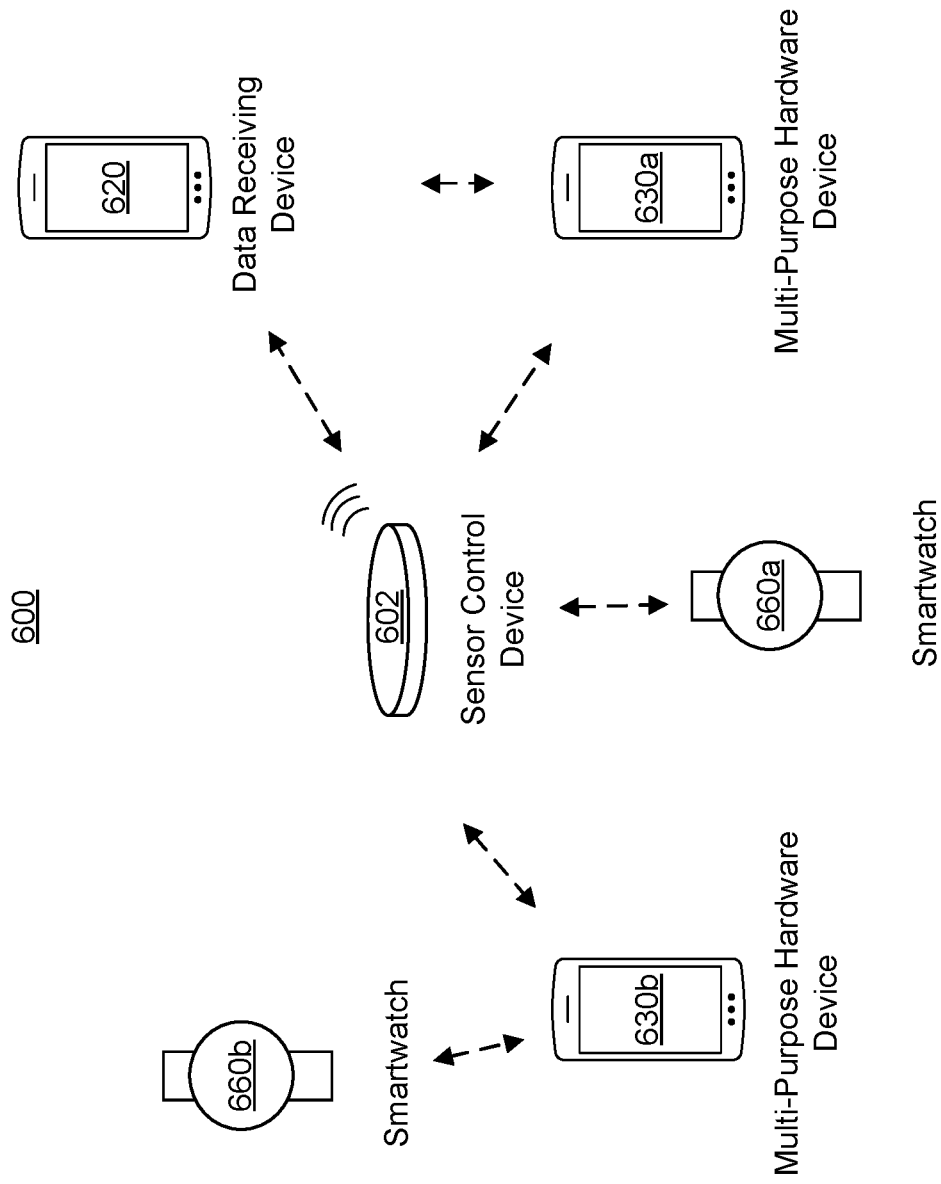

FIGS. 6A and 6B illustrate example embodiments of an operating environment of an analyte monitoring system 600 capable of embodying the techniques described herein. As illustrated, the analyte monitoring system 600 can include a system of components designed to provide monitoring of parameters, such as analyte levels, of a human or animal body or can provide for other operations based on the configurations of the various components. As embodied herein, the system can include a low-power sensor control device 602 worn by the user or attached to the body for which information is being collected. As embodied herein, the sensor control device 602 can be a sealed, disposable device with a predetermined active use lifetime (e.g., 1 day, 14 days, 30 days, etc.). Sensor control devices 602 can be applied to the skin of the user body and remain adhered over the duration of the sensor lifetime or can be designed to be selectively removed and remain functional when reapplied. The low-power analyte monitoring system 600 can further include a data reading device 620 or multi-purpose hardware device 630 configured as described herein to facilitate retrieval and delivery of data, including analyte data, from the sensor control device 602.

As embodied herein, the analyte monitoring system 600 can include a software or firmware library or application provided, for example via a remote application server 655 or application storefront server, to a third-party and incorporated into a multi-purpose hardware device 630 such as a mobile phone, tablet, personal computing device, or other similar computing device capable of communicating with the sensor control device 602 over a communication link. Multi-purpose hardware can further include embedded devices, including, but not limited to insulin pumps or insulin pens, having an embedded library configured to communicate with the sensor control device 602.

Although the illustrated embodiments of the analyte monitoring system 600 include only one of each of the illustrated devices, this disclosure contemplates the analyte monitoring system 600 incorporate multiples of each components interacting throughout the system. For example and without limitation, as embodied herein, data receiving device 620 and/or multi-purpose hardware device 630 can include multiples of each. As embodied herein, multiple-purpose hardware devices 630 can communicate directly with sensor control device 602 as described herein. Additionally or alternatively, a data receiving device 620 can communicate with secondary data receiving devices 620 to provide analyte data, or visualization or analysis of the data, for secondary display to the user or other authorized parties.

Figure 7:
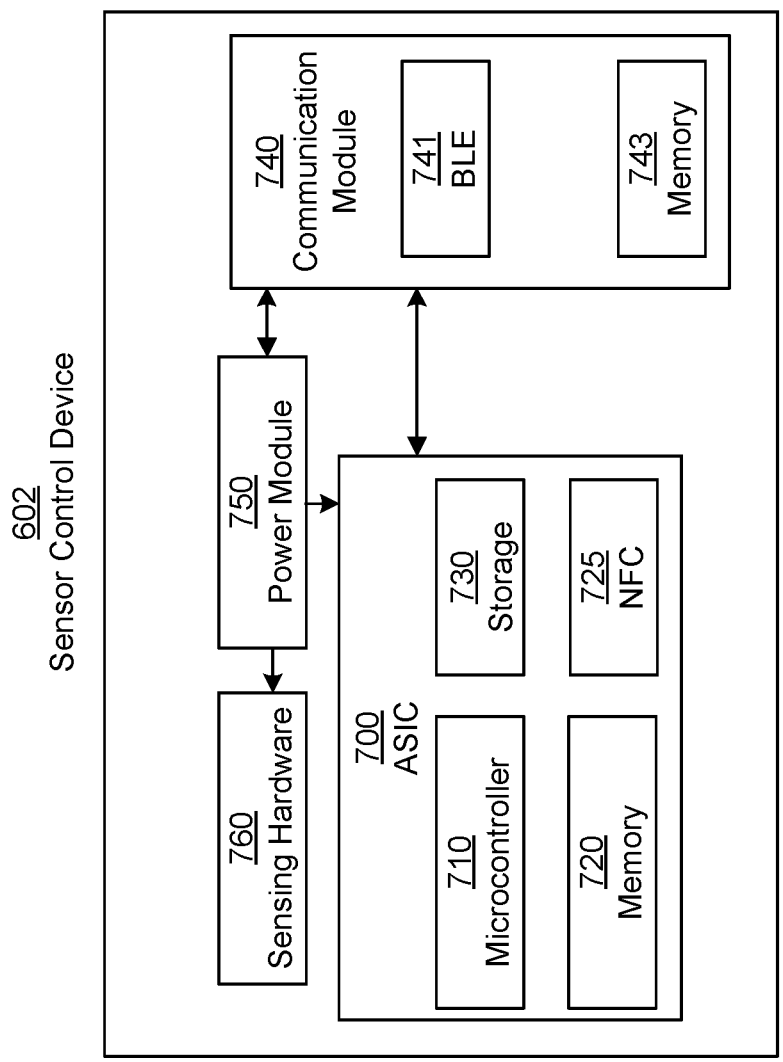
FIG. 7 is a block diagram illustrating an example sensor control device according to exemplary embodiments of the disclosed subject matter.

For purpose of illustration and not limitation, FIG. 7 depicts an exemplary embodiment of a sensor control device 602 compatible with the security architecture and communication schemes described herein.

As embodied herein, the sensor control device 602 can include an Application-Specific Integrated Circuit ("ASIC") 700 communicatively coupled with a communication module 740. The ASIC 700 can include a microcontroller core 710, on-board memory 720, and storage memory 730. The storage memory 730 can store data used in an authentication and encryption security architecture. The storage memory 730 can store programming instructions for sensor control device 602. As embodied herein, certain communication chipsets can be embedded in the ASIC 700 (e.g., an NFC transceiver 725). The ASIC 700 can receive power from a power module 750, such as an on-board battery or from an NFC pulse. The storage memory 730 of the ASIC 700 can be programmed to include information such as an identifier for sensor control device 602 for identification and tracking purposes. The storage memory 730 can also be programmed with configuration or calibration parameters for use by sensor control device 602 and its various components. The storage memory 730 can include rewritable or one-time programming (OTP) memory. The storage memory 730 can be updated using techniques described herein to extend the usefulness of sensor control device 602.

As embodied herein, the communication module 740 of sensor control device 602 can be or include one or more modules to support communications with other devices of an analyte monitoring system 600. As an example only, and not by way of limitation, example communication modules 740 can include a Bluetooth Low-Energy ("BLE") module 741 As used throughout this disclosure, BLE refers to a short-range communication protocol optimized to make pairing of Bluetooth devices simple for end users. The communication module 740 can transmit and receive data and commands via interaction with similarly-capable communication modules of a data receiving device 620 or user device 645. The communication module 740 can include additional or alternative chipsets for use with similar short-range communication schemes, such as a personal area network according to IEEE 802.15 protocols, IEEE 802.11 protocols, infrared communications according to the Infrared Data Association standards (IrDA), etc.

In particular embodiments, the communication module 740 or BLE module 741 can be or include the communication circuitry 200 described herein with respect to FIG. 2A.

To perform its functionalities, the sensor control device 602 can further include suitable sensing hardware 760 appropriate to its function. As embodied herein, the sensing hardware 760 can include an analyte sensor transcutaneously or subcutaneously positioned in contact with a bodily fluid of a subject. The analyte sensor can generate sensor data containing values corresponding to levels of one or more analytes within the bodily fluid. In particular embodiments, the sensing hardware 760 can include multiple analyte sensors, each cable of generating sensor data containing values corresponding to levels an analyte within the bodily fluid.

The storage memory 730 of the sensor control device 602 can include the software blocks related to communication protocols of the communication module. For example, the storage memory 730 can include a BLE services software block with functions to provide interfaces to make the BLE module 741 available to the computing hardware of the sensor control device 602. These software functions can include a BLE logical interface and interface parser. The software functions can include aspects of the BLE stack illustrated and discussed with respect to FIG. 2. BLE services offered by the communication module 740 can include the generic access profile service, the generic attribute service, generic access service, device information service, data transmission services, and security services. The data transmission service can be a primary service used for transmitting data such as sensor control data, sensor status data, analyte measurement data (historical and current), and event log data. The sensor status data can include error data, current time active, and software state. The analyte measurement data can include information such as current and historical raw measurement values, current and historical values after processing using an appropriate algorithm or model, projections and trends of measurement levels, comparisons of other values to patient-specific averages, calls to action as determined by the algorithms or models and other similar types of data.

According to aspects of the disclosed subject matter, and as embodied herein, a sensor control device 602 can be configured to communicate with multiple devices concurrently by adapting the features of a communication protocol or medium supported by the hardware and radios of the sensor control device 602. As an example, the BLE module 741 of the communication module 740 can be provided with software or firmware to enable multiple concurrent connections between the sensor control device 602 as a central device and the other devices as peripheral devices, or as a peripheral device where another device is a central device.

Connections, and ensuing communication sessions, between two devices using a communication protocol such as BLE can be characterized by a similar physical channel operated between the two devices (e.g., a sensor control device 602 and data receiving device 620). The physical channel can include a single channel or a series of channels, including for example and without limitation using an agreed upon series of channels determined by a common clock and channel- or frequency-hopping sequence. Communication sessions can use a similar amount of the available communication spectrum, and multiple such communication sessions can exist in proximity. In certain embodiment, each collection of devices in a communication session uses a different physical channel or series of channels, to manage interference of devices in the same proximity.

Data receiving device 620 can be a purpose-built device for receiving data from the sensor control device 602. Data receiving device 620 can be a mobile communication device such as, for example, a Wi-Fi or internet enabled smartphone, tablet, or personal digital assistant (PDA). Examples of smartphones can include, but are not limited to, those phones based on a WINDOWS operating system, ANDROID operating system, IPHONE operating system, PALM, WEBOS, BLACKBERRY operating system, or SYMBIAN operating system, with data network connectivity functionality for data communication over an internet connection and/or a local area network (LAN).

Data receiving device 620 can also be configured as a mobile smart wearable electronics assembly, such as an optical assembly that is worn over or adjacent to the user's eye (e.g., a smart glass or smart glasses, such as GOOGLE GLASSES). This optical assembly can have a transparent display that displays information about the user's analyte level (as described herein) to the user while at the same time allowing the user to see through the display such that the user's overall vision is minimally obstructed. The optical assembly can be capable of wireless communications similar to a smartphone. Other examples of wearable electronics include devices that are worn around or in the proximity of the user's wrist (e.g., a smart watch, etc.), neck (e.g., a necklace, etc.), head (e.g., a headband, hat, etc.), chest, or the like.

Figure 8:
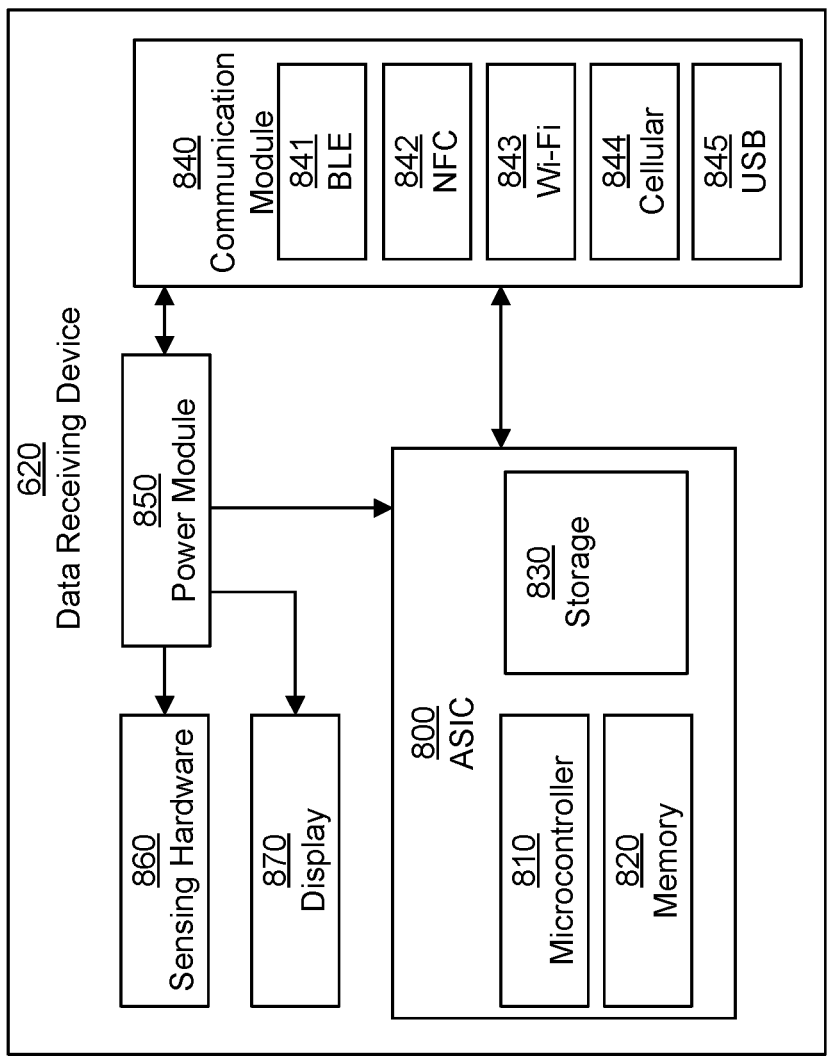
FIG. 8 is a block diagram illustrating an example data receiving device for communicating with the sensor control device according to exemplary embodiments of the disclosed subject matter.

For purpose of illustration and not limitation, reference is made to another exemplary embodiment of a data receiving device 620 for use with the disclosed subject matter as shown in FIG. 8. The data receiving device 620, and the related multi-purpose hardware device 630, includes components germane to the discussion of the sensor control device 602 and its operations and additional components can be included. In particular embodiments, the data receiving device 620 and multi-purpose hardware device 630 can be or include components provided by a third party and are not necessarily restricted to include devices made by the same manufacturer as the sensor control device 602.

As illustrated in FIG. 8, the data receiving device 620 includes an ASIC 800 including a microcontroller 810, memory 820, and storage 830 and communicatively coupled with a communication module 840. Power for the components of the data receiving device 620 can be delivered by a power module 850, which as embodied herein can include a rechargeable battery. The data receiving device 620 can further include a display 870 for facilitating review of analyte data received from an sensor control device 602 or other device (e.g., user device 645 or remote application server 655). The data receiving device 620 can include separate user interface components (e.g., physical keys, light sensors, microphones, etc.).

The communication module 840 can include a BLE module 841 and an NFC module 842. The data receiving device 620 can be configured to wirelessly couple with the sensor control device 602 and transmit commands to and receive data from the sensor control device 602. As embodied herein, the data receiving device 620 can be configured to operate, with respect to the sensor control device 602 as described herein, as an NFC scanner and a BLE end point via specific modules (e.g., BLE module 842 or NFC module 843) of the communication module 840. For example, the data receiving device 620 can issue commands (e.g., activation commands for a data broadcast mode of the sensor; pairing commands to identify the data receiving device 620) to the sensor control device 602 using a first module of the communication module 840 and receive data from and transmit data to the sensor control device 602 using a second module of the communication module 840. The data receiving device 620 can be configured for communication with a user device 645 via a Universal Serial Bus (USB) module 845 of the communication module 840.

As another example, the communication module 840 can include, for example, a cellular radio module 844. The cellular radio module 844 can include one or more radio transceivers for communicating using broadband cellular networks, including, but not limited to third generation (3G), fourth generation (4G), and fifth generation (5G) networks. Additionally, the communication module 840 of the data receiving device 620 can include a Wi-Fi radio module 843 for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)). Using the cellular radio module 844 or Wi-Fi radio module 843, the data receiving device 620 can communicate with the remote application server 655 to receive analyte data or provide updates or input received from a user (e.g., through one or more user interfaces). Although not illustrated, the communication module 740 of the analyte sensor 620 can similarly include a cellular radio module or Wi-Fi radio module.

In particular embodiments, the communication module 840 or BLE module 841 can be or include the communication circuitry 200 described herein with respect to FIG. 2A.

As embodied herein, the on-board storage 830 of the data receiving device 620 can store analyte data received from the sensor control device 602. Further, the data receiving device 620, multi-purpose hardware device 630, or a user device 645 can be configured to communicate with a remote application server 655 via a wide area network. As embodied herein, the sensor control device 602 can provide data to the data receiving device 620 or multi-purpose hardware device 630. The data receiving device 620 can transmit the data to the user computing device 645. The user computing device 645 (or the multi-purpose hardware device 630) can in turn transmit that data to a remote application server 655 for processing and analysis.

As embodied herein, the data receiving device 620 can further include sensing hardware 860 similar to, or expanded from, the sensing hardware 760 of the sensor control device 602. In particular embodiments, the data receiving device 620 can be configured to operate in coordination with the sensor control device 602 and based on analyte data received from the sensor control device 602. As an example, where the sensor control device 602 is a glucose sensor, the data receiving device 620 can be or include an insulin pump or insulin injection pen. In coordination, the compatible device can adjust an insulin dosage for a user based on glucose values received from the analyte sensor.

For purpose of illustration and not limitation, reference is made to an exemplary embodiment of a procedure for a sensor-receiver connection for use with the disclosed subject matter. First, the sensor control device 602 repeatedly advertises its connection information to its environment in a search for a data receiving device 620. The sensor control device 602 can repeat advertising on a regular basis until a connection established. The data receiving device 620 detects the advertising packet and scans and filters for the sensor control device 602 to connect to through the data provided in the advertising packet. Next, data receiving device 620 sends a scan request command and the sensor control device 602 responds with a scan response packet providing additional details. Then, the data receiving device 620 sends a connection request using the Bluetooth device address associated with the data receiving device 620. The data receiving device 620 can also continuously request to establish a connection to a sensor control device 602 with a specific Bluetooth device address. Then, the devices establish an initial connection allowing them to begin to exchange data. The devices begin a process to initialize data exchange services and perform a mutual authentication procedure.

During a first connection between the sensor control device 602 and data receiving device 620, the data receiving device 620 can initialize a service, characteristic, and attribute discovery procedure. The data receiving device 620 can evaluate these features of the sensor control device 602 and store them for use during subsequent connections. Next, the devices enable a notification for a customized security service used for mutual authentication of the sensor control device 602 and data receiving device 620. The mutual authentication procedure can be automated and require no user interaction. Following the successful completion of the mutual authentication procedure, the sensor control device 602 sends a connection parameter update to request the data receiving device 620 to use connection parameter settings preferred by the sensor control device 602 and configured to maximum longevity.

The data receiving device 620 then performs sensor control procedures to backfill historical data, current data, event log, and factory data. As an example, for each type of data, the data receiving device 620 sends a request to initiate a backfill process. The request can specify a range of records defined based on, for example, the measurement value, timestamp, or similar, as appropriate. The sensor control device 602 responds with requested data until all previously unsent data in the memory of the sensor control device 602 is delivered to the data receiving device 620. The sensor control device 602 can respond to a backfill request from the data receiving device 620 that all data has already been sent.

Once backfill is completed, the data receiving device 620 can notify sensor control device 602 that it is ready to receive regular measurement readings. The sensor control device 602 can send readings across multiple notifications result on a repeating basis. As embodied herein, the multiple notifications can be redundant notifications to ensure that data is transmitted correctly. Alternatively, multiple notifications can make up a single payload.

As embodied herein a first layer of security for communications between the sensor control device 602 and other devices can be established based on security protocols specified by and integrated in the communication protocols used for the communication. Another layer of security can be based on communication protocols that necessitate close proximity of communicating devices. Furthermore certain packets and/or certain data included within packets can be encrypted while other packets and/or data within packets is otherwise encrypted or not encrypted. Additionally or alternatively, application layer encryption can be used with one or more block ciphers or stream ciphers to establish mutual authentication and communication encryption with other devices in the analyte monitoring system 600.

The ASIC 700 of the sensor control device 602 can be configured to dynamically generate authentication and encryption keys using data retained within the storage memory 730. The storage memory 730 can also be pre-programmed with a set of valid authentication and encryption keys to use with particular classes of devices. The ASIC 700 can be further configured to perform authentication procedures with other devices using received data and apply the generated key to sensitive data prior to transmitting the sensitive data. The generated key can be unique to the sensor control device 602, unique to a pair of devices, unique to a communication session between a sensor control device 602 and other device, unique to a message sent during a communication session, or unique to a block of data contained within a message.

Both the sensor control device 602 and a data receiving device 620 can ensure the authorization of the other party in a communication session to, for example, issue a command or receive data. In particular embodiments, identity authentication can be performed through two features. First, the party asserting its identity provides a validated certificate signed by the manufacturer of the device or the operator of the analyte monitoring system 600. Second, authentication can be enforced through the use of public keys and private keys, and shared secrets derived therefrom, established by the devices of the analyte monitoring system 600 or established by the operator of the analyte monitoring system 600. To confirm the identity of the other party, the party can provide proof that the party has control of its private key.

The manufacturer of the sensor control device 602, data receiving device 620, or provider of the application for multi-purpose hardware device 630 can provide information and programming necessary for the devices to securely communicate through secured programming and updates. For example, the manufacturer can provide information that can be used to generate encryption keys for each device, including secured root keys for the sensor control device 602 and optionally for the data receiving device 620 that can be used in combination with device-specific information and operational data (e.g., entropy-based random values) to generate encryption values unique to the device, session, or data transmission as need.

Analyte data associated with a user is sensitive data at least in part because this information can be used for a variety of purposes, including for health monitoring and medication dosing decisions. In addition to user data, the analyte monitoring system 600 can enforce security hardening against efforts by outside parties to reverse-engineering. Communication connections can be encrypted using a device-unique or session-unique encryption key. Encrypted communications or unencrypted communications between any two devices can be verified with transmission integrity checks built into the communications. Sensor control device 602 operations can be protected from tampering by restricting access to read and write functions to the memory 720 via a communication interface. The sensor can be configured to grant access only to known or "trusted" devices, provided in a "whitelist" or only to devices that can provide a predetermined code associated with the manufacturer or an otherwise authenticated user. A whitelist can represent an exclusive range, meaning that no connection identifiers besides those included in the whitelist will be used, or a preferred range, in which the whitelist is searched first, but other devices can still be used. The sensor control device 602 can further deny and shut down connection requests if the requestor cannot complete a login procedure over a communication interface within a predetermined period of time (e.g., within four seconds). These characteristics safeguard against specific denial of service attacks, and in particular against denial of service attacks on a BLE interface.

As embodied herein, the analyte monitoring system 600 can employ periodic key rotation to further reduce the likelihood of key compromise and exploitation. A key rotation strategy employed by the analyte monitoring system 600 can be designed to support backward compatibility of field-deployed or distributed devices. As an example, the analyte monitoring system 600 can employ keys for downstream devices (e.g., devices that are in the field or cannot be feasibly provided updates) that are designed to be compatible with multiple generations of keys used by upstream devices.

For purpose of illustration and not limitation, reference is made to a demonstration and example exchange of data between a pair of devices, particularly a sensor control device 602 and a data receiving device 620. The data receiving device 620 can, as embodied herein, be a data receiving device 620 or a multi-purpose hardware device 630. The data receiving device 620 can transmit a sensor activation command to the sensor control device 602, for example via a short-range communication protocol. The sensor control device 602 can, prior to receiving the sensor activation command be in a primarily dormant state, preserving its battery until full activation is needed. After activation, the sensor control device 602 can collect data or perform other operations as appropriate to the sensing hardware 760 of the sensor control device 602. The data receiving device 620 can then initiate an authentication request command. In response to the authentication request command, both the sensor control device 602 and data receiving device 620 can engage in a mutual authentication process. The mutual authentication process can involve the transfer of data, including challenge parameters that allow the sensor control device 602 and data receiving device 620 to ensure that the other device is sufficiently capable of adhering to an agreed-upon security framework described herein. Mutual authentication can be based on mechanisms for authentication of two or more entities to each other with or without on-line trusted third parties to verify establishment of a secret key via challenge-response. Mutual authentication can be performed using two-, three-, four-, or five-pass authentication, or similar versions thereof.

Following a successful mutual authentication process, the sensor control device 602 can provide the data receiving device 620 with a sensor secret. The sensor secret can contain sensor-unique values and be derived from random values generated during manufacture. The sensor secret can be encrypted prior to or during transmission to prevent third-parties from accessing the secret. The sensor secret can be encrypted via one or more of the keys generated by or in response to the mutual authentication process. The data receiving device 620 can derive a sensor-unique encryption key from the sensor secret. The sensor-unique encryption key can further be session-unique. As such, the sensor-unique encryption key can be determined by each device without being transmitted between the sensor control device 602 or data receiving device 620. The sensor control device 602 can encrypt data to be included in payload. The sensor control device 602 can transmit the encrypted payload to the data receiving device 620 using the communication link established between the appropriate communication modules of the sensor control device 602 and data receiving device 620. The data receiving device 620 can decrypt the payload using the sensor-unique encryption key. The sensor control device 602 can deliver additional (including newly collected) data and the data receiving device 620 can process the received data appropriately.

As discussed herein, the sensor control device 602 can be a device with restricted processing power, battery supply, and storage. The encryption techniques used by the sensor control device 602 (e.g., the cipher algorithm or the choice of implementation of the algorithm) can be selected based at least in part on these restrictions. The data receiving device 620 can be a more powerful device with fewer restrictions of this nature. Therefore, the data receiving device 620 can employ more sophisticated, computationally intense encryption techniques, such as cipher algorithms and implementations.

The sensor control device 602 can be configured to alter its discoverability behavior to attempt to increase the probability of the receiving device receiving an appropriate data packet and/or provide an acknowledgment signal or otherwise reduce restrictions that can be causing an inability to receive an acknowledgment signal. Altering the discoverability behavior of the sensor control device 602 can include, for example and without limitation, altering the frequency at which connection data is included in a data packet, altering how frequently data packets are transmitted generally, lengthening or shortening the broadcast window for data packets, altering the amount of time that the sensor control device 602 listens for acknowledgment or scan signals after broadcasting, including directed transmissions to one or more devices (e.g., through one or more attempted transmissions) that have previously communicated with the sensor control device 602 and/or to one or more devices on a whitelist, altering a transmission power associated with the communication module when broadcasting the data packets (e.g., to increase the range of the broadcast or decrease energy consumed and extend the life of the battery of the analyte sensor), altering the rate of preparing and broadcasting data packets, or a combination of one or more other alterations. Additionally, or alternatively, the receiving device can similarly adjust parameters relating to the listening behavior of the device to increase the likelihood of receiving a data packet including connection data.

As embodied herein, the sensor control device 602 can be configured to broadcast data packets using two types of windows. The first window refers to the rate at which the sensor control device 602 is configured to operate the communication hardware. The second window refers to the rate at which the sensor control device 602 is configured to be actively transmitting data packets (e.g., broadcasting). As an example, the first window can indicate that the sensor control device 602 operates the communication hardware to send and/or receive data packets (including connection data) during the first 2 seconds of each 60 second period. The second window can indicate that, during each 2 second window, the sensor control device 602 transmits a data packet every 60 milliseconds. The rest of the time during the 2 second window, the sensor control device 602 is scanning. The sensor control device 602 can lengthen or shorten either window to modify the discoverability behavior of the sensor control device 602.

In particular embodiments, the discoverability behavior of the analyte sensor can be stored in a discoverability profile, and alterations can be made based on one or more factors, such as the status of the sensor control device 602 and/or by applying rules based on the status of the sensor control device 602. For example, when the battery level of the sensor control device 602 is below a certain amount, the rules can cause the sensor control device 602 to decrease the power consumed by the broadcast process. As another example, configuration settings associated with broadcasting or otherwise transmitting packets can be adjusted based on the ambient temperature, the temperature of the sensor control device 602, or the temperature of certain components of communication hardware of the sensor control device 602. In addition to modifying the transmission power, other parameters associated with the transmission capabilities or processes of the communication hardware of the sensor control device 602 can be modified, including, but not limited to, transmission rate, frequency, and timing. As another example, when the analyte data indicates that the subject is, or is about to be, experiencing a negative health event, the rules can cause the sensor control device 602 to increase its discoverability to alert the receiving device of the negative health event.

Data transmitted between the sensor control device 602 and a data receiving device 620 can include raw or processed measurement values. Data transmitted between the sensor control device 602 and data receiving device 620 can further include alarms or notification for display to a user. The data receiving device 620 can display or otherwise convey notifications to the user based on the raw or processed measurement values or can display alarms when received from the sensor control device 602. Alarms that can be triggered for display to the user include alarms based on direct analyte values (e.g., one-time reading exceeding a threshold or failing to satisfy a threshold), analyte value trends (e.g., average reading over a set period of time exceeding a threshold or failing to satisfy a threshold; slope); analyte value predictions (e.g., algorithmic calculation based on analyte values exceeds a threshold or fails to satisfy a threshold), sensor alerts (e.g., suspected malfunction detected), communication alerts (e.g., no communication between sensor control device 602 and data receiving device 620 for a threshold period of time; unknown device attempting or failing to initiate a communication session with the sensor control device 602), reminders (e.g., reminder to charge data receiving device 620; reminder to take a medication or perform other activity), and other alerts of a similar nature. For purpose of illustration and not limitation, as embodied herein, the alarm parameters described herein can be configurable by a user or can be fixed during manufacture, or combinations of user-settable and non-user-settable parameters.

FIG. 6B illustrates another embodiment of an operating environment of an analyte monitoring system 600 capable of embodying the techniques described herein. In particular, FIG. 6B illustrates the analyte monitoring system 600 including multiple and varied data receiving devices in communication with the sensor control device 602. Using the techniques described herein, the sensor control device 602 can maintain more than one simultaneous communications session with the various devices of the analyte monitoring system 600. As an example, the environment illustrated in FIG. 6B includes a second control device 602 in communication with a data receiving device 620, multiple multi-purpose hardware devices 630*a* and 630*b*, and additional monitoring devices, such as smartwatches 660*a* and 660*b*. Optionally, the sensor control device 602 maintains a direct connection with each of the receiving devices. As an example, illustrated in FIG. 6B, smartwatch 660*a* is in direct communication with the sensor control device 602. Optionally, data from the sensor control device 602 is relayed to a secondary receiving device, so that there is an indirect connection between the sensor control device 602 and the secondary receiving device. As an example, illustrated in FIG. 6B, smartwatch 660*b* is in communication with multi-purpose hardware device 630*b*, which is in turn in communication with sensor control device 602. Data and other communications from sensor control device 602 can be addressed to the smartwatch 660*b* and the multi-purpose hardware device 630*b* can detect these communications and appropriately relay them to the smartwatch 660*b*. Optionally, the communications from sensor control device 602 can be addressed to multi-purpose hardware device 630*b*, which in turn determines which communications should be relayed to the smartwatch 660*b*.

As described herein, the sensor control device 602 can maintain connections simultaneously with one or more of the receiving devices. The sensor control device 602 can determine which devices to which it will maintain a connection. Said determination can be based, for example, on a measure of signal or link quality between the sensor control device 602 and another device. Said determination can be based on a measure of priority of communications from the sensor control device 602. As an example, the sensor control device 602 can be preparing to send an urgent alarm related to the health of the user of the sensor control device 602. As an example, the sensor control device 602 can be configured to prioritize connecting and sending urgent alarm messages to a specific subset of receiving devices and can seek out a connection with these receiving devices first. Said determination can be based on the PHY supported by the received device. As an example, because the LE Coded 2S and LE Coded 8S PHYs support maintaining data connections through a more power efficient manner or over a longer range, the sensor control device 602 can prioritize maintaining connections with receiving devices that support these PHYs over maintaining connections with receiving devices that only support the LE 1M PHY. In certain embodiments, the number of receiving devices that the sensor control device 602 can maintain a connection with can be restricted based on the available memory of the sensor control device 602 to track these connections or based on restrictions in the communication protocol, for example.

As described previously, the operations relating to adaptively selecting a PHY to use for communications between host and peripheral devices can be applied to or by a data receiving device 620 and sensor control device 602. For the sake of brevity, and because the same analyses and operations can be used by the sensor control device 602 and data receiving device 620 when determining which PHY should be used and when the PHY should be change, the methods are not repeated in full here.

As described herein, the addition of support for various physical layers depending on the needs of a given communication session or communication environment, as well as the ability to adapt the communication in response to changes in the needs of the communication session or communication environment, enable medical devices, such as sensor control devices 602 and data receiving devices 620 (or other suitably configured multi-purpose hardware 630) to make and maintain communication sessions in more power efficient or useful manners. Using the techniques described herein, a sensor control device 602 or data receiving device 620, can select an appropriate physical layer to use for or during a communication session. For example, the data receiving device 620 can initially determine which physical layer to utilize during a communication session. Additionally or alternatively, the sensor control device 602, with which the data receiving device 620 communicates, can make the initial determination of the physical layer. Additionally or alternatively, the sensor control device 602 can determine that the initial physical layer designated for a communication session is not affording a sufficient level of performance or signal quality and instruct the data receiving device 620 or other receiving device to switch to a more reliable physical layer (e.g., switching from the LE 2M layer to the LE 1M or LE Coded layer). A similar determination can be made by the data receiving device 620.

Returning to FIG. 6B, in an environment in which the sensor control device 620 is maintaining a communication session with multiple devices, or has previously established communication sessions with multiple receiving devices, the connection pair can use or default to different physical layers. As an example, the sensor control device 620 can determine to use the LE Coded 8S PHY with multi-purpose hardware device 630a but to use the LE 1M PHY with smartwatch 660a (for example because the smartwatch 660a does not support additional physical layers). The sensor control device 620, using techniques similar to those describe above with respect to FIG. 5, can determine and store a default physical layer for each receiving device. The sensor control device 620 can further learn to use a new default physical layer based on changes in the communication environment, the pairing of the sensor control device 620 and the receiving device, or other characteristics.

As an example, the BLE module of the sensor control device 602 (or data receiving device 620) interfaces with a BLE module of a data receiving device 620 to transmit and receive telemetry data and information. In one example the BLE module monitors the communication link between the sensor control device 602 and a data receiving device 620 and records telemetry breaks, length of breaks, number of breaks in a given interval, time to reestablish a signal, signal to noise ratio, and the like. In this manner the BLE module can manage the communication link based on the quality or strength of a communication signal and amount or strength of local interference. The BLE module can select a new physical layer for the communication in response to changes in the communication link by, for example selecting an LE Coded PHY when the communication link reliability decreases (which may be due, for example, to increased interference or distance between the sensor control device 602 and the data receiving device 620) or selecting an LE 2M PHY in response to the communication link maintain a strong connection and an indication (as discussed above with respect to FIG. 4) that a faster data rate is preferable.

In addition, the sensor control device 602 may, based on the monitored communication quality, increase or decrease the power of a signal being transmitted. As an example, to conserve power, when the sensor control device 620 determines that link quality is stable and that a limited amount of data will be transmitted for a predetermined period of time, the sensor control device 620 can select to use an LE Coded PHY and reduce the transmission power of the communication session. In this way, the communication link can be maintained with a reduce current use, extending the life of the battery of the sensor control device 602.

As describe above with respect to FIG. 4, the sensor control device 602 or data receiving device 620, acting as host in a communication link, can determine the type of communication to occur and adapt the physical layer for the communication link accordingly. Nonlimiting examples of communication types may include alert communications (which can include varying levels of priority, such as urgent, high, medium, low, or system alerts), command communications, software updates, data transfers to backfill missing data and the like. In some embodiments, alert, command, and regular data type communications, from the sensor control device 602 in particular, can include relatively small amounts of information, also referred to as a small or smaller payload communications. As described herein, the sensor control device 602 can be configured to send analyte value readings from a preceding period of time to a data receiving device 620 on a regular, repeating basis. Each individual data packet is expected to be a relatively small payload communication.

Software update communications or data transfers to backfill missing data can include a relatively large amount of information, also referred to as large or larger payload communications. For example, a software update (including firmware updates) may modify, add, or replace algorithms used by the sensor control device 602. A backfill data transfer can be used to fill in missing data if the sensor control device 620 is not able to communicate regular data payloads to the data receiving device 620 over a period of time.

When considering whether to transition to a different physical layer, such as a higher data rate PHY (e.g., the LE 2M PHY) or lower data rate, more efficient PHY (e.g., an LE Coded PHY), the host device controlling the communication session can analyze the size of data transfer relative to the amount of time and/or current consumption required to adaptively select the PHY and complete the upload. In particular, the host device can consider whether the time and/or current expense to select a new PHY (e.g., the LE 2M PHY) and complete the data transfer using the higher data rate is actually greater than the time and/or current expense to use the current PHY. This analysis can include comparing the size of the data transfer to one or more thresholds, analyzing the type of data, the urgency of the data, the battery charge remaining in the sensor control device 602, and other factors. Similarly, the host device can analyze whether a relatively larger payload is anticipated to be delivered within a predetermined period of time when determining whether to use a lower data rate physical layer.

If only alert messages and regular data payloads are anticipated to be sent from the sensor control device 602 to the data receiving device 620, a lowest data rate can be applied as this type of transaction is not data heavy. In such embodiments, it may be considered more important and useful to the user to ensuring that a communication link is maintained between the sensor control device 602 and data receiving device 620 so that urgent alerts can be delivered.

As an example, a parent may have a first data receiving device 620 in communication with a sensor control device 602 implanted to a child. To enable the parent to continuously monitor the analyte levels of the child, sensor control device 602 and data receiving device 620 can select to use the LE Coded 8S PHY with the data rate set to, e.g., 125 Kb/s. The devices can adapt the transmission power based on monitoring the communication link quality to either conserve battery power (e.g., if the devices are in proximity) or to maximize effective transmission range. Therefore, using the techniques described herein, medical devices, such as those of an analyte monitoring system 600, can maintain a communication link over an extended range in comparison to using other techniques.

In certain embodiments, the physical layer for a communication link can be actively managed based on the battery life of the sensor control device 602 or data receiving device. Said embodiment can be particularly applicable in scenarios where both the sensor control device 602 and data receiving device 620 have relatively limited batteries (e.g., where the data receiving device is a smartwatch 660a). As an example, each device of a communication link can monitor its own remaining battery or expected battery depletion. If the remaining battery reaches a threshold amount, the device can request to enter into a power-savings communication mode in which it will use a reduced transmission power. Using the techniques of adaptable physical layers, the devices can reduce the impact of the reduced transmission power by switching to a lower data rate physical layer (e.g., the LE 1M PHY, LE Coded PHY) to ensure that regular data packets or alarm communications are still able to be received reliably. Additionally, an alarm can be sent, particularly by the sensor control device 602 indicating that the battery level is low and suggested actions to resolve the issue.

Additionally, maintaining an active communication link through adapting to or using a lower data rate physical layer such as an LE Coded PHY can expedite procedures if a larger payload is anticipated. As described herein, to maintain the confidentiality of transmitted data, the sensor control device 602 and data receiving device 620 can engage in a mutual authentication process when a new communication session is started. This mutual authentication process can further extend the delay before data is transmitted from the sensor control device 602 to the data receiving device 620. By maintaining an active communication link over a longer range (e.g., by using the LE Coded 8S PHY with a standard transmission power), the requirement of an additional mutual authentication procedure is obviated.

By utilizing the methodologies herein numerous advantages over other systems and methods are achieved. By utilizing a preferred PHY during communication sessions, a better user experience results including having a more robust communication link, more immunity to ambient interference, and experience fewer interruptions to the link. By utilizing PHY and power switching, the system and methodology allows the device to switch to lower power when the link quality is good or when a communication session is not active. Consequently, power consumption is decreased, resulting in increased operational life of medical devices, particularly small-format medical devices in which the battery is not necessarily replaceable.

While the foregoing embodiments are described in connection with the Bluetooth communications protocol, it is recognized that embodiments herein may be implemented in connection with other communications protocols that have multiple physical layers, where the multiple physical layers have different corresponding data rates, error detection or connection capabilities, signal qualities, power requirements and the like.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices, and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

In addition to the specific embodiments claimed below, the disclosed subject matter is also directed to other embodiments having any other possible combination of the dependent features claimed below and those disclosed above and in the attached figures. As such, the particular features disclosed herein can be combined with each other in other manners within the scope of the disclosed subject matter such that the disclosed subject matter can be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A medical device comprising: one or more processors;

one or more sensors configured to generate signals corresponding to one or more physiological signals detected in a body of a user;

a communication module comprising a transceiver configured to communicate wirelessly with a receiving device using a communication protocol capable of data transmission or reception at a plurality of data rates; and one or more memories communicatively coupled with the one or more processors, the one or more sensors, and the communication module, wherein the one or more memories comprise instructions to cause the one or more processors to:

transmit a communications packet to the receiving device, the communications packet representing at least one of an advertisement packet, a scan request packet, or a scan response packet, wherein the communications packet comprises information indicating that the communication module is configured to communicate using the plurality of data rates;

determine one of the plurality of data rates to be utilized for at least one of data transmission or reception during a communication session with the receiving device;

initialize the communication session with the receiving device using the determined data rate; and transmit, via the communication module to the receiving device and using the determined data rate, communications based on the signals corresponding to the one or more physiological signals, wherein at least one of:

i) the medical device is an implantable medical device configured to be implantable subcutaneously or ii) the one or more sensors comprise an analyte sensor configured a) to be at least partially implantable to collect an analyte generated by the body and b) to generate the signals corresponding to levels of the analyte in the body.

2. The medical device of claim 1, wherein the communication module is configured to receive a second communications packet from the receiving device, the second communications packet comprising an instruction designating the one of the data rates to be used during the communication session.

3. The medical device of claim 1, wherein the communication protocol is further capable of data transmission or reception at the plurality of data rates through the use of a plurality of physical layers.

4. The medical device of claim 3, wherein a first physical layer of the plurality of physical layers used by the communication protocol is a backwards-compatible physical layer, a second physical layer of the plurality of physical layers is a high data rate physical layer, and a third physical layer of the plurality of physical layers supports communication error correction.

5. The medical device of claim 3, wherein the communication protocol corresponds to a Bluetooth-enabled communication protocol, wherein the communication protocol is Bluetooth version 5.0 or higher.

6. The medical device of claim 5, wherein the first physical layer corresponds to a LE 1M physical layer, the second physical layer corresponds to a LE 2M physical layer, and the third physical layer corresponds to a LE Coded physical layer.

7. The medical device of claim 1, wherein the instructions further cause the one or more processors to receive, via the communication module and from the receiving device, second communications using a second data rate of the plurality of data rates.

8. The medical device of claim 1, wherein the instructions further cause the one or more processors to:
determine one of the plurality of data rates to be utilized for at least one of data transmission or reception during a second communication session with a second receiving device;
initialize the second communication session with the second receiving device using the determined data rate; and
transmit, via the communication module to the second receiving device and using the determined data rate, second communications based on the signals corresponding to the one or more physiological signals.

9. The medical device of claim 8, wherein the receiving device is a smartphone and the second receiving device is a smartwatch.

10. The medical device of claim 8, wherein the communication session with the receiving device and the second communication session with the second receiving device are maintained concurrently.

11. The medical device of claim 1, wherein the plurality of data rates comprises at least three different data rates.

12. The medical device of claim 1, wherein the determined data rate is utilized for data transmission during the communication session and a second data rate is utilized for data reception during the communication session.

13. A medical device
comprising: one or more processors;
one or more sensors configured to generate signals corresponding to one or more physiological signals detected in a body of a user;
a communication module comprising a transceiver configured to communicate wirelessly with a receiving device using a communication protocol capable of data transmission or reception at a plurality of data rates; and
one or more memories communicatively coupled with the one or more processors, the one or more sensors, and the communication module, wherein the one or more memories comprise instructions to cause the one or more processors to:
transmit information to the receiving device indicating that the communication module is configured to communicate using the plurality of data rates;
determine at least one of a type of communications to be transmitted to the receiving device or a size of a data set to be transmitted to the receiving device;
determine one of the plurality of data rates to be used for at least one of data transmission or reception during a communication session with the receiving device based on at least one of the type of communications or the size of the data set;
initialize the communication session with the receiving device using the determined data rate; and
transmit, via the communication module to the receiving device and using the determined data rate, communications based on the signals corresponding to the one or more physiological signals, wherein at least one of:
i) the medical device is an implantable medical device configured to be implantable subcutaneously or
ii) the one or more sensors comprise an analyte sensor configured a) to be at least partially implantable to collect an analyte generated by the body and b) to generate the signals corresponding to levels of the analyte in the body.

14. A medical device
comprising: one or more processors;
one or more sensors configured to generate signals corresponding to one or more physiological signals detected in a body of a user;
a communication module comprising a transceiver configured to communicate wirelessly with a receiving device using a communication protocol capable of data transmission or reception at a plurality of data rates through the use of a plurality of physical layers, wherein each data rate of the plurality of data rates corresponds to a physical layer of the plurality of physical layers; and
one or more memories communicatively coupled with the one or more processors, the one or more sensors, and the communication module, wherein the one or more memories comprise instructions to cause the one or more processors to:
transmit information to the receiving device indicating that the communication module is configured to communicate using the plurality of data rates;
determine one of the plurality of data rates to be utilized for at least one of data transmission or reception during a communication session with the receiving device; initialize the communication session with the receiving device using the determined data rate; and
transmit, via the communication module to the receiving device and using the determined data rate, communications based on the signals corresponding to the one or more physiological signals, wherein at least one of:
  i) the medical device is an implantable medical device configured to be implantable subcutaneously or
  ii) the one or more sensors comprise an analyte sensor configured a) to be at least partially implantable to collect an analyte generated by the body and b) to generate the signals corresponding to levels of the analyte in the body.

15. A medical device
comprising: one or more processors;
one or more sensors configured to generate signals corresponding to one or more physiological signals detected in a body of a user;
a communication module comprising a transceiver configured to communicate wirelessly with a receiving device using a communication protocol capable of data transmission or reception at a plurality of data rates; and
one or more memories communicatively coupled with the one or more processors, the one or more sensors, and the communication module, wherein the one or more memories comprise instructions to cause the one or more processors to:
  transmit information to the receiving device indicating that the communication module is configured to communicate using the plurality of data rates;
  determine one of the plurality of data rates to be utilized for at least one of data transmission or reception during a communication session with the receiving device; initialize the communication session with the receiving device using the determined data rate;
  transmit, via the communication module to the receiving device and using the determined data rate, communications based on the signals corresponding to the one or more physiological signals;
  after transmitting the communications to the receiving device using the determined data rate, determine a second of the plurality of data rates to be utilized for at least one of data transmission or reception during the communication session with the receiving device; and
  transmit, via the communication module to the receiving device and using the second determined data rate, second communications based on the signals corresponding to the one or more physiological signals, wherein at least one of:
    i) the medical device is an implantable medical device configured to be implantable subcutaneously or
    ii) the one or more sensors comprise an analyte sensor configured a) to be at least partially implantable to collect an analyte generated by the body and b) to generate the signals corresponding to levels of the analyte in the body.

16. The medical device of claim 15, wherein the determination of the second of the plurality of data rates is based on monitoring one or more connection criteria of the communication session, the connection criteria comprising a data throughput requirement, a communication type, a battery indicator, a telemetry break condition, or a link condition of the communication session between the medical device and the receiving device.

17. A medical device
comprising: one or more processors;
one or more sensors configured to generate signals corresponding to one or more physiological signals detected in a body of a user, wherein the one or more sensors comprise an analyte sensor configured a) to be at least partially implantable to collect an analyte generated by the body and b) to generate signals corresponding to levels of the analyte in the body of the user;
a communication module comprising a transceiver configured to communicate wirelessly with a receiving device using a communication protocol capable of data transmission or reception at a plurality of data rates; and
one or more memories communicatively coupled with the one or more processors, the one or more sensors, and the communication module, wherein the one or more memories comprise instructions to cause the one or more processors to:
  transmit information to the receiving device indicating that the communication module is configured to communicate using the plurality of data rates;
  determine one of the plurality of data rates to be utilized for at least one of data transmission or reception during a communication session with the receiving device; initialize the communication session with the receiving device using the determined data rate; and
  transmit, via the communication module to the receiving device and using the determined data rate, communications based on the signals corresponding to the one or more physiological signals.

18. A method of selecting one of a plurality of data rates for a wireless communication session between a medical device and a receiving device comprising:
  transmitting, by a communication module of the medical device, a communications packet to the receiving device, the communications packet representing at least one of an advertisement packet, a scan request packet, or a scan response packet, wherein the communications packet comprises information indicating that the communication module is configured to communicate using a communication protocol capable of data transmission or reception at the plurality of data rates, wherein the medical device further comprises one or more sensors configured to generate signals corresponding to one or more physiological signals detected in a body of a user;
  determining, by the medical device, one of the plurality of data rates to be utilized for at least one of data transmission or reception during the communication session with the receiving device;
  initializing, by the communication module, the communication session with the receiving device using the determined data rate; and
  transmitting, by the communication module to the receiving device and using the determined data rate, communications based on the signals corresponding to the one or more physiological signals, wherein at least one of:
    iii) the medical device is an implantable medical device configured to be implantable subcutaneously or
    iv) the one or more sensors comprise an analyte sensor configured a) to be at least partially implantable to collect an analyte generated by the body and b) to generate the signals corresponding to levels of the analyte in the body.

19. The method of claim 18, further comprising receiving, at the communication module, a second communications packet from the receiving device, the second communications packet comprising an instruction designating the one of the data rates to be used during the communication session.

20. The method of claim 18, wherein the communication protocol is further capable of data transmission or reception at the plurality of data rates through the use of a plurality of physical layers.

21. The method of claim 20, wherein a first physical layer of the plurality of physical layers used by the communication protocol is a backwards-compatible physical layer, a second physical layer of the plurality of physical layers is a high data rate physical layer, and a third physical layer of the plurality of physical layers supports communication error correction.

22. The method of claim 20, wherein the communication protocol corresponds to a Bluetooth-enabled communication protocol, wherein the communication protocol is Bluetooth version 5.0 or higher.

23. The method of claim 22, wherein the first physical layer corresponds to a LE 1M physical layer, the second physical layer corresponds to a LE 2M physical layer, and the third physical layer corresponds to a LE Coded physical layer.

24. The method of claim 18, further comprising receiving, via the communication module and from the receiving device, second communications using a second data rate of the plurality of data rates.

25. The method of claim 18, wherein the determining the one of the plurality of data rates is based on monitoring one or more connection criteria of the communication session, the connection criteria comprising a data throughput requirement, a communication type, a battery indicator, a telemetry break condition, or a link condition of the communication session between the medical device and the receiving device.

26. The method of claim 18, further comprising:
determining one of the plurality of data rates to be utilized for at least one of data transmission or reception during a second communication session with a second receiving device;
initializing the second communication session with the second receiving device using the determined data rate; and
transmitting, via the communication module to the second receiving device and using the determined data rate, second communications based on the signals corresponding to the one or more physiological signals.

27. The method of claim 26, wherein the receiving device is a smartphone and the second receiving device is a smartwatch.

28. The method of claim 26, wherein the communication session with the receiving device and the second communication session with the second receiving device are maintained concurrently.

29. The method of claim 18, wherein the plurality of data rates comprises at least three different data rates.

30. The method of claim 18, wherein the determined data rate is utilized for data transmission during the communication session and a second data rate is utilized for data reception during the communication session.

31. A method of selecting one of a plurality of data rates for a wireless communication session between a medical device and a receiving device comprising:
transmitting, by a communication module of the medical device, information to the receiving device indicating that the communication module is configured to communicate using a communication protocol capable of data transmission or reception at the plurality of data rates, wherein the medical device further comprises one or more sensors configured to generate signals corresponding to one or more physiological signals detected in a body of a user;
determining, by the medical device, at least one of a type of communications to be transmitted to the receiving device or a size of a data set to be transmitted to the receiving device;
determining, by the medical device, one of the plurality of data rates to be utilized for at least one of data transmission or reception during the wireless communication session with the receiving device based on at least one of the type of communications or the size of the data set;
initializing, by the communication module, the communication session with the receiving device using the determined data rate; and
transmitting, by the communication module to the receiving device and using the determined data rate, communications based on the signals corresponding to the one or more physiological signals, wherein at least one of:
i) the medical device is an implantable medical device configured to be implantable subcutaneously or
ii) the one or more sensors comprise an analyte sensor configured a) to be at least partially implantable to collect an analyte generated by the body and b) to generate the signals corresponding to levels of the analyte in the body.

32. A method of selecting one of a plurality of data rates for a wireless communication session between a medical device and a receiving device comprising:
transmitting, by a communication module of the medical device, information to the receiving device indicating that the communication module is configured to communicate using a communication protocol capable of data transmission or reception at the plurality of data rates through the use of a plurality of physical layers, wherein each data rate of the plurality of data rates corresponds to a physical layer of the plurality of physical layers, wherein the medical device further comprises one or more sensors configured to generate signals corresponding to one or more physiological signals detected in a body of a user; determining, by the medical device, one of the plurality of data rates to be utilized for at least one of data transmission or reception during the communication session with the receiving device;
initializing, by the communication module, the communication session with the receiving device using the determined data rate; and
transmitting, by the communication module to the receiving device and using the determined data rate, communications based on the signals corresponding to the one or more physiological signals, wherein at least one of:
i) the medical device is an implantable medical device configured to be implantable subcutaneously or
ii) the one or more sensors comprise an analyte sensor configured a) to be at least partially implantable to collect an analyte generated by the body and b) to generate the signals corresponding to levels of the analyte in the body.

33. A method of selecting one of a plurality of data rates for a wireless communication session between a medical device and a receiving device comprising:
transmitting, by a communication module of the medical device, information to the receiving device indicating that the communication module is configured to communicate using a communication protocol capable of data transmission or reception at the plurality of data rates, wherein the medical device further comprises one or more sensors configured to generate signals corresponding to one or more physiological signals detected in a body of a user;

determining, by the medical device, one of the plurality of data rates to be utilized for at least one of data transmission or reception during the communication session with the receiving device;

initializing, by the communication module, the communication session with the receiving device using the determined data rate;

transmitting, by the communication module to the receiving device and using the determined data rate, communications based on the signals corresponding to the one or more physiological signals;

after transmitting the communications to the receiving device using the determined data rate, determining a second of the plurality of data rates to be utilized for at least one of data transmission or reception during the communication session with the receiving device; and transmitting, by the communication module to the to the receiving device and using the second determined data rate, second communications based on the signals corresponding to the one or more physiological signals, wherein at least one of:
  i) the medical device is an implantable medical device configured to be implantable subcutaneously or
  ii) the one or more sensors comprise an analyte sensor configured a) to be at least partially implantable to collect an analyte generated by the body and b) to generate the signals corresponding to levels of the analyte in the body.

34. A method of selecting one of a plurality of data rates for a wireless communication session between a medical device and a receiving device comprising:

transmitting, by a communication module of the medical device, information to the receiving device indicating that the communication module is configured to communicate using a communication protocol capable of data transmission or reception at the plurality of data rates, wherein the medical device further comprises one or more sensors configured to generate signals corresponding or more physiological signals detected in a body of a user, wherein the one or more sensors comprise an analyte sensor configured a) to be at least partially implantable to collect an analyte generated by the body and b) to generate signals corresponding to levels of the analyte in the body of the user;

determining, by the medical device, one of the plurality of data rates to be utilized for at least one of data transmission or reception during the communication session with the receiving device;

initializing, by the communication module, the communication session with the receiving device using the determined data rate; and transmitting, by the communication module to the receiving device and using the determined data rate, communications based on the signals corresponding to the one or more physiological signals.

* * * * *